US009518283B1

(12) United States Patent
Olstein

(10) Patent No.: US 9,518,283 B1
(45) Date of Patent: *Dec. 13, 2016

(54) SELECTIVE ENRICHMENT MEDIA AND USES THEREOF

(71) Applicant: Paradigm Diagnostics, Inc., Chanhassen, MN (US)

(72) Inventor: Alan D. Olstein, Mendota Heights, MN (US)

(73) Assignee: Paradigm Diagnostics, Inc., Chanhassen, MN (US)

( * ) Notice: Subject to any disclaimer, the term of this patent is extended or adjusted under 35 U.S.C. 154(b) by 58 days.

This patent is subject to a terminal disclaimer.

(21) Appl. No.: 14/189,488

(22) Filed: Feb. 25, 2014

Related U.S. Application Data

(63) Continuation-in-part of application No. 13/778,192, filed on Feb. 27, 2013, now Pat. No. 9,029,118.

(60) Provisional application No. 61/769,785, filed on Feb. 27, 2013, provisional application No. 61/603,738, filed on Feb. 27, 2012.

(51) Int. Cl.
| | | |
|---|---|---|
| C12N 1/38 | (2006.01) | |
| C12Q 1/10 | (2006.01) | |
| C12Q 1/04 | (2006.01) | |

(52) U.S. Cl.
CPC .. *C12Q 1/10* (2013.01); *C12Q 1/04* (2013.01)

(58) Field of Classification Search
None
See application file for complete search history.

(56) References Cited

U.S. PATENT DOCUMENTS

| | | | |
|---|---|---|---|
| 4,279,995 A | 7/1981 | Woods et al. | |
| 5,098,832 A | 3/1992 | Rambach | |
| 5,194,374 A | 3/1993 | Rambach | |
| 5,208,150 A | 5/1993 | Tate et al. | |
| 5,434,056 A | 7/1995 | Monget et al. | |
| 5,789,188 A * | 8/1998 | Rothstein | C12N 15/52 435/252.3 |
| 5,871,944 A | 2/1999 | Miller et al. | |
| 5,989,832 A * | 11/1999 | Trias | A61K 31/167 435/29 |
| 6,368,817 B1 | 4/2002 | Perry et al. | |
| 7,150,977 B2 | 12/2006 | Restaino | |
| 7,704,706 B2 | 4/2010 | Druggan | |
| 7,829,543 B2 | 11/2010 | Nelson et al. | |
| 7,960,164 B2 | 6/2011 | Olstein | |

FOREIGN PATENT DOCUMENTS

EP  0209758 A2  6/1986

OTHER PUBLICATIONS

Von Baum et al. "Antimicrobial resistance of *Escherichia coli* and therapeutic implications", International Journal of Medical Microbiology 295 (6): 503-511, 2005.*
Murugkar et al. "Isolation, phage typing & antibiogram of Salmonella from man & animals in northeastern India", Indian Journal of Medical Research 122: 237-242, 2005.*
Achillies et al., "Analysis of living *S. cerevisiae* cell state-a three color approach", Cytometry Part A 69A: 173-7, 2006.
BD® "BD® Bionutrients™ Technical Manual: Advance Bioprocessing", 3rd Edition, available online on company's webpage, Oct. 2006.
Bohnert et al., *Selected Arylpiperazines are Capable of Reversing Multidrug Resistance in Escherichia coli Overexpressing RND Efflux Pumps*, Antimicrob. Agents & Chemoth. 49(2):849-852 (2005).
Christensen, et al., *Regulation of Expression of the 2-Deoxy-D-Ribose Utilization Regulon, deoQKPX, from Salmonella enteric Serovar Typhimurium*. J. Bact. 185(20):6042-6050 (2003).
Cold Spring Harbor Protocols "LB (Luria-Bertanie) liquid medium", Cold Spring Harbor Protocols, available online, 2006.
Corrente et al., "Isolation of Salmonella strains from reptile faeces and comparison of different culture media", Journal of Applied Microbioloty 96: 709-15, 2004.
Frech et al. *Molecular analysis of tetracycline resistance in Salmonella enteric subsp. Enteric serovars Typhimurium, enteritides, Dublin, Choleraesuis, Hadar and Saintpaul: construction and application of specific gene probes* Journal of Applied Microbiology 89: 633-641, 2000.
Hanson et al., *Recommended Test Panel for Differentiation of Klebsiella Species on the Basis of a Trilateral Interlaboratory Evaluation of 18 Biochemical Tests*. J. Clin. Microbiol. 42(8):3665-3669 (2004).
Hoben et al. "Some observations on the incorporation of novobiocin into Hektoen enteric agar for improved Salmonella isolation", Applied Microbioloty 26(1): 126-7, 1973.
Kaatz, GW, et al., *Phenylpiperidine selective serotonin reuptake inhibitors interfere with multidrug efflux pump activity in Staphylococcus aureus*,Int J Antimicrob Agents 2003;22:254-61.
Kern, WB., et al., *Effect of 1-(1-naphthylmethyl)-piperazine, a novel putative efflux pump inhibitor, on antimicrobial drug susceptibility in clinical isolates of Escherichia coli*, J Antimicrob Chemother; 57: 339-343, 2006.
Koronakis, V., *TolC—the bacterial exit duct for proteins and drugs*,FEBS Lett 2003;555-66-71.
Levy, SB, *Active efflux, a common mechanism for biocide and antibiotic resistance*,J Appl Microbiol 2002;92 Suppl:65-71.
Li, et al., *Efflux-medicated drug resistance in bacteria*, Drugs 2004;64:159-204.
Li, et al., *Efflux-medicated drug resistance in bacteria: an update*, Drugs 69(12):1555-1623, 2009.
Lomovskaya, et al., *Vacuuming the periplasm*, J. Bacteriol 2005;187:1879-83.

(Continued)

*Primary Examiner* — Emily Cordas
(74) *Attorney, Agent, or Firm* — Daniel Blasiole; Charles Sara, Esq.; DeWitt Ross & Stevens SC

(57) ABSTRACT

Selective enrichment media and methods for selectively growing and detecting *Salmonella* spp. and/or Shiga toxin-producing *E. coli*. The media may comprise a carbon and nitrogen source, an inorganic salt, a fermentable sugar, one or more selective agents, and an efflux pump inhibitor. Various selective agents include sulfa drugs, surfactants, aminocoumarins, cycloheximide, supravital stains, ascorbic acid, bromobenzoic acid, myricetin, nitrofurantoin, rifamycins, polyketides, and oxazolidinones. Various efflux pump inhibitors include arylpiperazines, such as 1-(1-naphthylmethyl)piperazine, and quinoline derivatives, such as 4-chloroquinoline. Methods of selectively growing and detecting *Salmonella* and/or Shiga toxin-producing *E. coli* are provided.

18 Claims, No Drawings

(56) References Cited

OTHER PUBLICATIONS

Lomovskaya, et al., *Practical applications and feasibility of efflux pump inhibitors in the clinic—a vision for applied use,* Biochem Pharmacol 2006;71:910-18.

Mead, et al., *Food-related illness and death in the United States.* Emerg. Infect. Dis. 5:607-625. (1999).

Mahamoud, et al., *Antibiotic efflux pumps in Gram-negative bacteria: the inhibitor response strategy,* J. Antimicrob. Chemoth. 59(6): 1223-1229 (2007).

Mahamoud, A., et al., *Quinolone derivatives as promising inhibitors of antibiotic efflux pump in multidrug resistant Enterobacter aerogenes,* Curr Drug Targets 2006,7:843-7.

Manafi et al. "*New developments in chromogenic and fluorogenic culture media*" International Journal of Food Microbiology 60: 205-18, 2000.

Moats et al., "*Factors affecting selectivity of brillian green-phenol red agar for Samonellae*", Applied and Environmental Microbioloty 27(1): 118-123, 1974.

Molnar, J., et al., *Inhibition of the transport function of membrane proteins by some substituted phenothiazines in E. coli and multidrug resistant tumor cells,*Anticancer Res 1997;17:481-6.

Nakayama, K. et al., *MexAB-OprM-specific efflux pump inhibitors in Pseudomonas aeruginos. Part 1: discovery and early strategies for lead optimization,* Bioorg Med Chem Lett 2003;13:4201-4.

Nakayama, K. et al., *MexAB-OprM-specific efflux pump inhibitors in Pseudomonas aeruginos. Part 2: achieving activity in vivo through the use of alternative scaffolds,* Bioorg Med Chem Lett 2003;13:4205-8.

Nakayama, K. et al., *MexAB-OprM-specific efflux pump inhibitors in Pseudomonas aeruginos. Part 3: Optmization of potency in the pyridopyrimidine series through the application of a pharmacophore model,* Bioorg Med Chem Lett 2004;14:475-9.

Nakayama, K. et al., *MexAB-OprM-specific efflux pump inhibitors in Pseudomonas aeruginos. Part 4:Addressing the problem of poor stability due to photoisomerization of an acrylic acid moiety,* Bioorg Med Chem Lett 2004;14:2493-7.

Nakayama, K. et al., *MexAB-OprM-specific efflux pump inhibitors in Pseudomonas aeruginos. Part 5: Carbon-substituted analogues at the C-2 position,* Bioorg Med Chem Lett 2006;14:1993-2004.

Nelson, ML et al., *Inhibition of the tetracycline efflux antiport protein by 13-thio-submitted 5-hydroxy-6-deoxytetracyclines,* J Med Chem 1993;36: 370-377.

Nelson, ML et al., *Molecular requirements for the inhibition of the tetracycline antiport protein and the effect of potent inhibitors on the growth of tetracycline-resistant bacteria,* J Med Chem 1994;37:1355-61.

Pannek, S. et al., *Multidrug efflux inhibition in Acinetobacter baumannii: comparison between 1-(1-naphthylmethyl)-piperazine and phenyl-arginine-beta-naphthylamide,* J Antimcrob Chemother 2006;57:970-4.

Paulson, IT, *Multidrug efflux pumps and resistance: regulation and evolustion,*Curr Opin Microbiol 2003;6:446-51.

Piddock, *Clinically Relevant Chromosomally Encoded Multidrug Resistance Efflux Pumps in Bacteria,* Clin. Microbiol. Rev. 19(2): 382-402 (2006).

Piddock et al., "*Natural and synthetic compounds such as trimethoprim behave as inhibitors of efflux in gram-negative bacteria*", Journal of Antimicrobial chemotherapy 65: 1215-1223, 2010.

Pool, K., *Efflux-mediated antimicrobial resistance,*J Antimicrob Chemother 2005;56:20-51.

Puupponen-Pimia et al., "*Antimicrobial properties of phenolic compounds from berries*", Journal of Applied Microbiology 90: 494-507, 2001.

Saier, MH Jr., *Tracing pathways of transport protein evoluation,* 'Mol. Microbiol 2003;48:1145-56.

Schumacher, et al., *Effect of 1-(1-naphthylmethyl)-piperazine, a novel putative efflux pump inhibitor, on antimicrobial drug susceptibility in clinical isolates of Enterobacteriacae other than E. coli,* J. Antimicrob. Chemother 2006;57:344-8.

Sigma® "*Yeast Nitrogen Base Product information*", available online. 2012.

Thorarensen, A., et al., *3-Arylpiperidines as potentiators of existing antibacterial agents,* Bioorg Med Chem Lett 2001;11:1903-6.

Tourneux, et al., *Genetic and Biochemical Characterization of Salmonella enteric Serovar Typhi Deoxyribokinase,* J. Bact. 182(4):869-873 (2000).

Van Bambeke, et al., *Antibiotic efflux pumps in prokaryotic cells: occurrence, impact on resistance and strategies for the future of antimicrobial therapy,* J Antimicrob chemother 2003;51:1055-65.

Van Bambeke, et al., *Inhibitors of Bacterial Efflux Pumps as Adjuvants in Antibiotic Treatments and Diagnostic Tools for Detection of Resistance by Efflux,* Frontiers in Anti-Infective Drug Discovery, 2010, 1, 138-175.

U.S. Food and Drug Administration (2011) *Bacteriological Analytical Manual,* Chapter 5, www.fda.gov/food/scienceresearch/laboratorymethods/bacteriologicalanalyticalmanual.BAM/USC070149.

http://www.biology.ucsd.edu/-msaier/transport.

\* cited by examiner

SELECTIVE ENRICHMENT MEDIA AND USES THEREOF

CROSS-REFERENCE TO RELATED APPLICATIONS

This application claims priority under 35 USC §119(e) to U.S. Provisional Patent Application 61/769,785, filed Feb. 27, 2013, and is a continuation-in-part of U.S. patent application Ser. No. 13/778,192, filed Feb. 27, 2013, which claims priority under 35 USC §119(e) to U.S. Provisional Patent Application 61/603,738, filed Feb. 27, 2012, the entireties of all which are incorporated herein by reference.

FIELD OF THE INVENTION

The invention is directed to selective enrichment and indicator media. The invention is more specifically directed to the use of bacterial efflux pump inhibitors to enhance the selectivity of selective enrichment media for the isolation and detection of certain microorganisms, such as Salmonella species and/or Shiga toxin-producing E. coli strains.

BACKGROUND

Foodborne salmonellosis is a major public health problem. Salmonella is the second leading cause of annual foodborne illness cases, with an estimated 1,340,000 cases compared with nearly 2,000,000 for Campylobacter. A survey conducted in the United States estimated that in 1999 non-typhoidal salmonellosis of foodborne origin caused approximately 15,600 hospitalizations and 550 deaths (Mead, P. S., L. Slutsker, V. Dietz, et al. Food-related illness and death in the United States. Emerg. Infect. Dis. 5:607-625. 1999). Although the genus Salmonella has more than 2300 serovars, only a relatively restricted number belonging mainly to the enterica subspecies of the Salmonella enterica species are responsible for the great majority of human infections. The most common sources of Salmonella infections in humans are contaminated foods, including eggs, poultry, produce, meat, and meat products. Eggs and poultry meat are recognized as the major vehicles of human infections because of epizootics in fowl.

Early detection of foodborne Salmonella is vital for food safety assurance. However, conventional methods for detecting foodborne Salmonella are laborious and time consuming. These methods typically involve identifying presumptively positive samples by sequentially processing samples in a pre-enrichment phase, a selective-enrichment phase, and then an analysis phase. The analysis phase may involve culturing the enriched sample on selective differential agar, analyzing with polymerase chain reaction (PCR), and/or analyzing via immunoassay. After identifying the presumptively positive samples, confirmation of the presumptively positive samples typically requires biochemical characterization of isolates obtained from selective, differential agar media. See, e.g., U.S. Food and Drug Administration (2011) Bacteriological Analytical Manual, Chapter 5. It is estimated that millions of such Salmonella analyses are run routinely in the United States each year.

Early detection of Salmonella is needed if foodborne illnesses caused by Salmonella are to be reduced. While determinative microbiology requires confirmation of presumptively positive samples, this is not the case in many applications such as environmental monitoring and food safety-HACCP testing. In such applications, only a reasonable presumption that a sample is contaminated is required to take such corrective actions as modifying a sanitation procedure or quarantining a product lot pending subsequent confirmation. Rapid screening tests which have comparable diagnostic performance to culture methods or other rapid molecular methods can suffice.

Several Salmonella-selective enrichment media and systems are known in the art. See, e.g., U.S. Pat. No. 4,279,995 to Woods et al.; U.S. Pat. No. 5,208,150 to Tate et al.; U.S. Food and Drug Administration (2011) Bacteriological Analytical Manual, Chapter 5; U.S. Pat. No. 7,704,706 to Druggan; U.S. Pat. No. 7,150,977 to Restaino; U.S. Pat. No. 6,368,817 to Perry et al.; U.S. Pat. No. 5,434,056 to Monget et al.; and U.S. Pat. No. 5,194,374 to Rambach. The media and systems described in these references do not provide sufficient selectivity of Salmonella spp.

Another major cause of foodborne illness is Shiga toxin-producing E. coli (STEC). STEC has been linked with the severe complication hemolytic-uremic syndrome (HUS) and other deleterious outcomes. Shiga toxin-producing E. coli is known by a number of other names, including enterohemorrhagic E. coli (EHEC), Shiga-like toxin-producing E. coli (SLTEC), hemolytic uremic syndrome-associated enterohemorrhagic E. coli (HUSEC), and verocytotoxin- or verotoxin-producing E. coli (VTEC).

All the Shiga toxin-producing E. coli strains produce Shiga toxin (also known as, Shiga-like toxin or verotoxin), a major cause of foodborne illness. EHEC strains are distinguished from commensal E. coli. Shiga toxin-producing E. coli strains can be distinguished from non-Shiga toxin-producing E. coli strains by detecting the Shiga toxin genes (Stx1 and/or Stx2) in E. coli or the gene products thereof. See, e.g., Chassagne L, Pradel N, Robin F, Livrelli V, Bonnet R, Delmas J. Detection of stx1, stx2, and eae genes of enterohemorrhagic Escherichia coli using SYBR Green in a real-time polymerase chain reaction. Diagn Microbiol Infect Dis. 2009 May; 64(1):98-101.

The best known of Shiga toxin-producing E. coli strains is O157:H7, but non-O157 strains cause an estimated 36,000 illnesses, 1,000 hospitalizations and 30 deaths in the United States yearly. Food safety specialists recognize the "Big Six" Shiga toxin-producing E. coli strains: O26, O45, O103, O111, O121, and O145. A 2011 outbreak in Germany was caused by another Shiga toxin-producing E. coli strain, O104:H4. This strain has both enteroaggregative and enterohemorrhagic properties. Both the O145 and O104 strains can cause hemolytic-uremic syndrome. The former strain was shown to account for 2% to 51% of known HUS cases. An estimated 56% of such cases are caused by O145 and 14% by other Shiga toxin-producing E. coli strains.

Shiga toxin-producing E. coli strains that induce bloody diarrhea lead to HUS in 10% of cases. The clinical manifestations of postdiarrheal HUS include acute renal failure, microangiopathic hemolytic anemia, and thrombocytopenia. The Shiga toxin can directly damage renal and endothelial cells. Thrombocytopenia occurs as platelets are consumed by clotting. Hemolytic anemia results from intravascular fibrin deposition, increased fragility of red blood cells, and fragmentation.

An important trend in the meat industry in the United States is the ability to cultivate E. coli and Salmonella in the same selective enrichment media. Laboratories would like to streamline their processes by reducing the steps to regulatory compliance to one operation for screening for both pathogenic E. coli and Salmonella.

There exists a need for a simple, rapid screening test that identifies presumptively positive Salmonella and/or Shiga toxin-producing E. coli samples at an early stage of the sample analysis, preferably in a selective enrichment stage of the analysis. Simultaneous enrichment and detection of *Salmonella* and/or Shiga toxin-producing *E. coli* using a single testing method would reduce not only time but also the cost of labor and media. Streamlining procedures and reducing labor and test costs should permit more frequent monitoring for Shiga toxin-producing *E. coli*, thereby reducing contamination hazard.

SUMMARY OF THE INVENTION

The present invention provides selective enrichment media for *Salmonella* species such as *Salmonella enterica*, and/or Shiga toxin-producing *E. coli*. The present invention also provides selective indicator broths that simultaneously enrich and detect *Salmonella* and/or Shiga toxin-producing *E. coli* within a sample. The selective indicator broths incorporate metabolic indicators that produce a visually detectable signal, such as a color change, as *Salmonella* species or Shiga toxin-producing *E. coli* strains grow in the media and ferment the substrates or optionally hydrolyze chromogenic substrates such as Xgal, etc. The media of the invention incorporate selectively targeted inhibitors to prevent growth by background micro-flora and, hence, metabolism of the indicator substrates, thereby preventing undesirable false positive responses.

The present invention provides selective enrichment media capable of suppressing the growth of *Klebsiella, Enterobacter, Citrobacter*, and commensal *E. coli* species without compromising the growth of *Salmonella enterica* and/or Shiga toxin-producing *E. coli* by incorporating efflux pump inhibitors (EPIs) in the media. One of the principal mechanisms by which bacteria have evolved to defeat toxic compounds in the environment is the presence of proteins in bacterial membranes capable of pumping these compounds out of the intracellular space. These proteins, known as efflux pumps, reside in both cytoplasmic and outer membrane structures of certain bacteria (Piddock, L. J. *Clinically Relevant Chromosomally Encoded Multidrug Resistance Efflux Pumps in Bacteria*. Clin. Microbiol. Rev. 19(2): 382-402. 2006). Various classes of both natural and synthetic compounds can inhibit these efflux pumps. Some inhibitors are highly active across the Enterobacteriacae family in preventing the ejection of numerous antibiotics. For example, the peptidomimetic compound Phe-Arg-β-naphthylamide has been demonstrated to be effective in many gram-negative bacteria, including *E. coli* and *Salmonella enterica* (Piddock, L. J. *Clinically Relevant Chromosomally Encoded Multidrug Resistance Efflux Pumps in Bacteria*. Clin. Microbiol. Rev. 19(2): 382-402. 2006). Some of the arylpiperazines and alkylquinolines appear to be more limited in their spectrum of action (Bohnert, J. et al. Selected Arylpiperazines Are Capable of Reversing Multidrug Resistance in *Escherichia coli* Overexpressing RND Efflux Pumps. *Antimicrob. Agents & Chemoth.* 49(2):849-852. 2005; Schumacher, A. et al. Effect of 1-(1-naphthylmethyl)-piperazine, a novel putative efflux pump inhibitor, on antimicrobial drug susceptibility in clinical isolates of Enterobacteriacae other than *E. coli. J. Antimicrob. Chemoth.* 57: 344-348. 2005; and Mahamoud, A. et al. Antibiotic efflux pumps in Gram-negative bacteria: the inhibitor response strategy. *J. Antimicrob. Chemoth.* 59(6):1223-1229. 2007).

The present invention employs antibiotics and EPIs that enable selective enrichment for *Salmonella* and/or Shiga toxin-producing *E. coli*. It has been found that neither arylpiperazines nor alkylquinolines increase the susceptibility of *Salmonella enterica* or Shiga toxin-producing *E. coli* to the several antibiotics known to be rendered effective against other gram negative bacteria such as *Enterobacter* spp. and commensal *E. coli*. The resistance of *Salmonella enterica* and Shiga toxin-producing *E. coli* to the antibiotic-sensitizing effects of arylpiperazines and alkylquinolines forms the basis of at least some versions of the selective enrichment media of the present invention. These media are more selective for *Salmonella* than those currently in use, such as Rapaport-Vasiliadis medium and tetrathionate broth (U.S. Food and Drug Administration (2011) *Bacteriological Analytical Manual*, Chapter 5).

An exemplary selective enrichment medium of the invention comprises a carbon and nitrogen source, an inorganic salt, a selective agent, and an efflux pump inhibitor. The selective agent preferably comprises one or more of a sulfa drug, a surfactant, an aminocoumarin, cycloheximide, myricetin, nitrofurantoin, a rifamycin, a polyketide, and an oxazolidinone.

The efflux pump inhibitor may comprise one or more of a phenothiazine, a phenylpiperidine, a tetracycline analog, an aminoglycoside analog, a fluoroquinolone analog, a quinoline derivative, a peptidomimetic, a pyridopyrimidine, an arylpiperidine, and an arylpiperazine. The efflux pump inhibitor preferably comprises one or more of an arylpiperazine and a quinoline derivative. In some versions, the efflux pump inhibitor may comprise 1-(1-naphthylmethyl)piperazine. In some versions, the efflux pump inhibitor may comprise 4-chloroquinoline.

Some media include 2-deoxy-D-Ribose as a fermentable sugar.

Some media include one or more of sulfanilamide and sulfathiazole as a sulfa drug. Sulfanilamide and sulfathiazole may be included in the media in a ratio of about 9:1.

Some media include 7-ethyl-2-methyl-4-undecyl sulfate or a salt thereof as a selective agent.

Some media include novobiocin as an aminocoumarin.

Some media include rifampicin as a rifamycin.

Some media include one or more of tetracycline and doxycycline as a polyketide.

Some media include linezolid as an oxazolidinone.

Some media include a fermentable sugar. The fermentable sugar may include 2-deoxy-D-Ribose.

Some media include a supravital stain. The supravital stain may comprise brilliant green.

Some media include ascorbic acid.

Some media include bromobenzoic acid.

Some media include one or more of a rifamycin, a polyketide, and an oxazolidinone as a selective agent, and one or more of an arylpiperazine and a quinoline derivative as an efflux pump inhibitor.

Some media include one or more of rifampicin, tetracycline, doxycycline, and linezolid as a selective agent, and one or more of 1-(1-naphthylmethyl)piperazine and 4-chloroquinoline as an efflux pump inhibitor.

Some media include a sulfa drug, a surfactant, an aminocoumarin, cycloheximide, myricetin, and nitrofurantoin as a selective agent, and further include one or more of an arylpiperazine and a quinoline derivative as an efflux pump inhibitor.

Some media include a sulfa drug, a surfactant, an aminocoumarin, cycloheximide, myricetin, nitrofurantoin, and one or more of a rifamycin, a polyketide, and an oxazolidinone as a selective agent, and further include one or more of an arylpiperazine and a quinoline derivative as an efflux pump inhibitor.

Some media include a visual indicator that indicates the presence of a microorganism selected from the group consisting of *Salmonella* and *E. coli*.

The selective agent and the efflux pump inhibitor may be present in amounts effective to inhibit growth of at least one non-*Salmonella* species to a greater extent than one or more *Salmonella* species. The selective agent and the efflux pump inhibitor are also preferably present in amounts effective to inhibit growth of at least one non-*Salmonella* species while not substantially inhibiting growth of one or more *Salmonella* species.

The selective agent and the efflux pump inhibitor may be present in amounts effective to inhibit growth of at least one non-Shiga toxin-producing *E. coli* strain to a greater extent than one or more Shiga toxin-producing *E. coli* strains. The selective agent and the efflux pump inhibitor are also preferably present in amounts effective to inhibit growth of at least one non-Shiga toxin-producing *E. coli* strain while not substantially inhibiting growth of one or more Shiga toxin-producing *E. coli* strains.

The components of the media are preferably present in amounts that permit growth of *E. coli* having a type selected from O157, O145, O104, O26, O111, O103, and O91.

The media of the invention may be in a liquid form, i.e., a broth, or may be in solid or semi-solid form, e.g., agar-based.

The invention also provides for methods of selectively enriching for a microorganism selected from the group consisting of *Salmonella* and Shiga toxin-producing *E. coli*. The methods comprise culturing a sample suspected of containing *Salmonella* and/or Shiga toxin-producing *E. coli* in selective enrichment media as described herein. The culturing preferably grows *Salmonella*, Shiga toxin-producing *E. coli*, or both *Salmonella* and Shiga toxin-producing *E. coli*, such as at least one *Salmonella* species, at least one Shiga toxin-producing *E. coli* strain, or at least one *Salmonella* species and at least one Shiga toxin-producing *E. coli* strain. In some versions, the culturing grows *Salmonella enterica*. In some versions, the culturing grows *E. coli* having a type selected from O157, O145, O104, O26, O111, O103, and O91. Further, the culturing preferably substantially inhibits growth of a microorganism selected from the group consisting of *Citrobacter* spp. and non-Shiga toxin-producing *E. coli*, such as at least one *Citrobacter* sp. and/or at least one non-Shiga toxin-producing *E. coli* strain. The methods may further comprise detecting presence of the microorganism, such as *Salmonella*, Shiga toxin-producing *E. coli*, or both *Salmonella* and Shiga toxin-producing *E. coli*, such as at least one *Salmonella* species, at least one Shiga toxin-producing *E. coli* strain, or at least one *Salmonella* species and at least one Shiga toxin-producing *E. coli* strain.

The objects and advantages of the invention will appear more fully from the following detailed description of the preferred embodiment of the invention.

DETAILED DESCRIPTION OF THE INVENTION

The various components of the media of the present invention are described as follows.

The media of the invention preferably include a carbon and nitrogen source. Preferred carbon and nitrogen sources include protein hydrolysates and/or extracts. Suitable carbon and nitrogen sources include peptone, neopeptone, tryptone, beef extract paste, desiccated powder of beef heart, desiccated powder of beef liver, brain heart infusion, digests of casein, and yeast extract. Examples include the following products from BD (Franklin Lakes N.J.): ACIDICASE™ Peptone (hydrochloric acid hydrolysis of casein; Cat. No. 211843); Beef Extract Paste (Cat. No. 212610); Beef Heart for Infusion (Desiccated powder of beef heart, Cat. No. 213210); BIOSATE™ Peptone (Cat No. 211862); BIOSATE™ Peptone (Cat. No. 294312); Brain Heart Infusion (Cat. No. 237300); Casamino acids (acid hydrolyzed casein; Cat. Nos. 223050, 223020, 223120, 223030, 223110, 228820, 228830, and 228830); Casein Digest (Enzymatic digest of casein for molecular genetics, Cat. No. 211610); Casitone (Pancreatic digest of casein; Cat. Nos. 225930 and 225910); Gelatin (Cat. Nos. 214340 and 214320); GELYSATE™ Peptone (Pancreatic digest of gelatin; Cat. No. 211870); Liver (Desiccated powder of beef liver; Cat. No. 213320); Neopeptone (Enzymatic digest of protein; Cat. Nos. 211680 and 211681); Peptone (An enzymatic digest of protein; Cat Nos. 211830, 211677, 254820, 211820); PHYTONE™ Peptone (An enzymatic digest of soybean meal, Non-animal origin; Cat. Nos. 211906 and 298147); PHYTONE™ Peptone UF (Ultra-filtered enzymatic digest of soybean meal, designed specifically for cell culture applications, non-animal origin; Cat. Nos. 210931 and 210936); Polypeptone Peptone (Pancreatic digest of casein and peptic digest of animal tissue combined in equal parts; Cat. Nos. 211910 and 297108); Proteose Peptone (Enzymatic digest of protein, high in proteoses; Cat. Nos. 212010, 253310, and 211684); Proteose Peptone No. 2 (Enzymatic digest of protein; Cat. Nos. 212120 and 212110); Proteose Peptone No. 3 (Enzymatic digest of protein; Cat. Nos. 211693, 211692, 212220, and 212230) Proteose Peptone No. 4 (Enzymatic digest of protein; Cat. No. 211715); Select Soytone (Enzymatic digest of soybean meal, non-animal origin; Cat. Nos. 212489 and 212488); Soytone, BACTO™ (Enzymatic hydrolysate of soybean meal; Cat. Nos. 243620 and 243610); TC Yeastolate (Water soluble portion of autolyzed yeast, source of Vitamin B complex, tested for tissue culture; Cat. Nos. 255772 and 255771); TRYPTICASE™ Peptone (Enzymatic digest of casein; Cat. No. 211921); TRYPTICASE™ Peptone (Enzymatic digest of casein; Cat. Nos. 211922 and 211923); Tryptone (Enzymatic digest of casein; Cat. Nos. 211705, 211701, and 211699); Tryptone, BITEK™ (Enzymatic digest of casein; Cat. No. 251420); Tryptose (Enzymatic hydrolysate of protein; Cat. Nos. 211709 and 211713); Yeast Extract (Water-soluble extract of autolyzed yeast cells suitable for use in culture media; Cat. Nos. 212720, 211931, 211929, 212710, 212730, 211930, and 212750); Yeast Extract, LD (Water-soluble extract of autolyzed yeast cells that has been agglomerated to minimize dusting; Cat. Nos. 210933 and 210941); Yeast Extract, UF (Water-soluble extract of autolyzed yeast cells, ultrafiltration enhances solubility and lowers the endotoxin, suitable for use in cell culture and microbial fermentation; Cat. Nos. 210934 and 210929); and equivalents thereof. Peptone or tryptone supplemented with beef or yeast extract are preferred carbon and nitrogen sources. Suitable concentration ranges of the carbon and nitrogen source are from about 1 g/L to about 300 g/L, preferably about 2 g/L to about 150, and most preferably from about 10 g/L to about 30 g/L.

The media of the invention may include an inorganic salt. Suitable inorganic salts include calcium salts, copper salts, iron salts, selenium salts, potassium salts, magnesium salts, sodium salts, ammonium salts, nickel salts, tin salts, and zinc salts, among others. Suitable examples of such salts include $CaCl_2$, $CuSO_4$, $FeSO_4$, $H_2SeO_3$, KCl, KI, $KH_2PO_4$, $MgCl_2$, $MgCO_3$, $MgSO_4$, $MnSO_4$, $Na_2HPO_4$, $Na_2SiO_3$, NaCl, $NaH_2PO_4$, $NaHCO_3$, $NH_4VO_3$, $(NH_4)_6MO_7O_{24}$, NiCl$_2$, SnCl$_2$, ZnSO$_4$, and hydrates thereof. Magnesium, potassium, calcium, iron and/or zinc salts are preferred. Magnesium salts, such as magnesium chloride (MgCl$_2$), magnesium carbonate (MgCO$_3$), magnesium sulfate (MgSO$_4$), and hydrates thereof are particularly preferred. A particularly suitable magnesium salt is magnesium chloride. The inorganic salt is preferably included at a concentration sufficient to create high osmotic pressure in the medium. Suitable concentration ranges of the inorganic salt are from about 0.1 g/L to about 50 g/L, preferably about 2 g/L to about 40 g/L, more preferably from about 4 g/L to about 35 g/L, and most preferably from about 6 g/L to about 15 g/L.

The media of the invention may include a pH indicator. The pH indicator is preferably sensitive to acidification. The pH indicator is preferably an indicator that transitions color in a range of about pH 7 to about pH 5. Examples of suitable pH indicators are bromocresol purple, phenol red, and neutral red. Bromocresol purple is preferred. The pH indicator may be included in any concentration suitable for detecting the pH change. Exemplary ranges include about 0.004 g/L to about 0.25 g/L, such as about 0.02 g/L to about 0.05 g/L.

The media of the invention may include a fermentable sugar. Examples of suitable sugars include adonitol, arabinose, arabitol, ascorbic acid, 5-bromo-4-chloro-3-indolyl-β-D-galactopyranoside (X-gal), chitin, D-cellubiose, 2-deoxy-D-ribose, dulcitol, (S)-(+)-erythrulose, fructose, fucose, galactose, glucose, isopropyl β-D-1-thiogalactopyranoside (IPTG), inositol, lactose, lactulose, lyxose, maltitol, maltose, maltotriose, mannitol, mannose, melezitose, melibiose, microcrystalline cellulose, palatinose, pentaerythritol, raffinose, rhamnose, ribose, sorbitol, sorbose, starch, sucrose, trehalose, xylitol, xylose, and hydrates thereof. For selection of *Salmonella* spp., it is preferred to use a sugar that can be efficiently metabolized by *Salmonella* spp. but not by other bacteria. 2-Deoxy-D-ribose, xylose, mannitol, dulcitol, sorbitol, L-rhamnose and D-arabitol are suitable for this purpose. 2-Deoxy-D-ribose is particularly preferred because of its relative selectivity toward *Salmonella enterica*. It was previously thought that, with the exception of a few *Citrobacter* species, most non-*Salmonella* species within Enterobacteriacae are incapable of fermenting 2-deoxy-D-ribose (Tourneux, L. et al. Genetic and Biochemical Characterization of *Salmonella enterica* Serovar *Typhi* Deoxyribokinase. *J. Bact.* 182(4):869-873. 2000; and Christensen, M. et al. Regulation of Expression of the 2-Deoxy-D-Ribose Utilization Regulon, deoQKPX, from *Salmonella enterica* Serovar *Typhimurium*. J. Bact. 185(20):6042-6050. 2003). However, more recent publications have provided evidence that some *Klebsiella* and *Enterobacter* species can also ferment 2-Deoxy-D-ribose (Hansen et al. Recommended Test Panel for Differentiation of *Klebsiella* Species on the Basis of a Trilateral Interlaboratory Evaluation of 18 Biochemical Tests. *J. Clin. Microbiol.* 42(8):3665-3669. 2004). The fermentable sugar may be included in the media at a concentration of from about 0.5 g/L to about 120 g/L, preferably of from about 1.0 g/L to about 60 g/L, and more preferably of from about 5.0 to about 12.0 g/L.

The media of the invention may include one or more visual indicators. "Visual indicators" as used herein denote components that provide a visual indication of the presence of one or more types of microorganisms. The media of the invention preferably include one or more visual indicators that indicate the presence of *Salmonella*; *E. coli*, such as Shiga toxin-producing *E. coli*; or both *Salmonella* and *E. coli*. Exemplary indicators include the combination of bromocresol purple and 2-deoxy-D-ribose for indicating the presence of *Salmonella*, and the combination of 5-bromo-4-chloro-3-indolyl-β-D-galactopyranoside (X-gal) and isopropyl β-D-1-thiogalactopyranoside (IPTG) for indicating the presence of *E. coli* and other lactose-positive coliforms. Other visual indicators for indicating the presence of *Salmonella*, *E. coli*, and other microorganisms are known in the art.

The media of the invention may include one or more selective agents described below, or otherwise known in the art. Each selective agent may be included in an amount effective to inhibit growth of at least one non-*Salmonella* microorganism and/or at least one non-Shiga toxin-producing *E. coli* microorganism to a greater extent than *Salmonella* (such as *Salmonella enterica*) and/or Shiga toxin-producing *E. coli* (such as *E. coli* having a type selected from O157, O145, O104, O26, O111, O103, and O91). It is preferred that the one or more selective agents are present in amounts that do not substantially inhibit the growth or metabolism of *Salmonella* (such as *Salmonella enterica*) and/or Shiga toxin-producing *E. coli* (such as *E. coli* having a type selected from O157, O145, O104, O26, O111, O103, and O91).

The media of the invention may include one or more sulfa drugs as a selective agent. The sulfa drug serves as an anti-metabolite selective agent. Sulfa drugs, also called sulfonamides or sulphonamides, are antimicrobial agents that contain the sulfonamide group. Examples of suitable sulfa drugs include aldesulfone sodium, elixir sulfanilamide, mafenide, phthalylsulfathiazole, prontosil, silver sulfadiazine, succinylsulfathiazole, sulfabenzamide, sulfacetamide, sulfacytine, sulfadiazine, sulfadicramide, sulfadimethoxine, sulfadimidine, sulfadoxine, sulfafurazole, sulfaguanidine, sulfalene, sulfamazone, sulfamerazine, sulfamethizole, sulfamethoxazole, sulfamethoxypyridazine, sulfametomidine, sulfametoxydiazine, sulfametrole, sulfamoxole, sulfanilamide, sulfaperin, sulfaphenazole, sulfapyridine, sulfaquinoxaline, sulfathiazole, sulfathiourea, sulfatolamide, and sulfisomidine, among others. Sulfathiazole is preferably included because of its toxicity to some *Citrobacter* spp. A preferred combination of sulfa drugs includes sulfanilamide and sulfathiazole in a ratio of about 9:1, such as in concentrations of about 0.9 g/L and 0.1 g/L, respectively. The one or more sulfa drugs may be included in the media at a concentration of from about 0.05 g/L to about 20 g/L, more preferably of from about 0.1 g/L to about 10 g/L, and most preferably from about 0.5 g/L to about 2.0 g/L. Such concentrations refer to the total concentration of all sulfa drugs in the composition. The media of the invention may contain one or more surfactants as a selective agent. The surfactant may be a non-ionic surfactant, an ionic surfactant, or an amphoteric surfactant. If an ionic surfactant, the surfactant may be a cationic surfactant or an anionic surfactant. Preferred surfactants are anionic surfactants, such as aliphatic sulfates. The aliphatic sulfate may have a branched aliphatic chain or a linear aliphatic chain. Preferred aliphatic sulfates include 7-ethyl-2-methyl-4-undecanol hydrogen sulfate or sodium salt thereof (Tergitol 4; CAS No. 139-88-8) and 7-ethyl-2-methyl-4-undecyl sulfate or sodium salt thereof (NIAPROOF® 4, available under Cat. No. N1404 from Sigma-Aldrich Co., St. Louis, Mo.). The 7-ethyl-2-methyl-4-undecyl sulfate or a sodium salt thereof is particularly preferred. These aliphatic sulfates inhibit growth of *Proteus* spp. The one or more surfactants may be included in the media at a concentration of from about 0.1 g/L to about 45 g/L, preferably of from about 0.2 g/L to about 22.5 g/L, and more preferably of from about 1.0 g/L to about 4.5 g/L.

The media of the invention may contain one or more aminocoumarins as a selective agent. Aminocoumarins include clorobiocin, coumermycin A1, and novobiocin. Novobiocin is a preferred aminocoumarin for inclusion in the media of the invention. Novobiocin is a Gram-positive antibacterial. Novobiocin appears to facilitate *Salmonella* spp. recovery in selective enrichment media, probably by inhibiting the growth of competitive microorganisms. The one or more aminocoumarins may be included in the media at a concentration of from about 0.002 g/L to about 1 g/L, preferably about 0.004 g/L to about 0.5 g/L, and more preferably about 0.02 g/L to about 0.10 g/L.

The media of the invention may contain cycloheximide as a selective agent. Cycloheximide is an inhibitor of protein biosynthesis in eukaryotic organisms and thereby inhibits the growth of mold and yeast. Addition of cycloheximide is useful, as some yeasts can ferment 2-deoxy-D-ribose. The cycloheximide may be included in the media at a concentration of from about 0.001 g/L to about 1.0 g/L, preferably of from about 0.002 g/L to about 0.5 g/L, and more preferably of from about 0.01 g/L to about 0.10 g/L.

The media of the invention may contain a supravital stain as a selective agent. As used herein, "supravital stain" refers to a stain that enters and stains living cells, such as bacteria. Such stains are toxic to certain organisms over time, some more so than others. Examples of supravital stains include gentian violet, crystal violet, brilliant green, bismark brown, safranin, methylene blue, and malachite blue, among others. Preferred supravital stains include those that are more highly toxic to non-*Salmonella* microorganisms and/or non-Shiga toxin-producing *E. coli* microorganisms than *Salmonella* and/or non-Shiga toxin-producing *E. coli*. Brilliant green is a preferred supravital stain for including the media. Brilliant green is a trimethylaryl dye that inhibits certain non-*Salmonella* Gram-negative and Gram-positive bacteria. Brilliant green inhibits many commensal *E. coli* but surprisingly has no effect against Shiga toxin-producing *E. coli* at concentrations of about 1 mg/L. Brilliant green bleaches at low pH and therefore does not interfere with the pH indicator reaction. Other supravital stains, such as malachite blue, do not bleach effectively at low pH and would therefore preclude the use of a chromogenic pH indicator. Such supravital stains, however, may be used when an indication of a change in pH is not desired or needed. The supravital stain may be included in the media at a concentration of from about 0.0001 g/L to about 0.5 g/L, preferably of from about 0.0002 g/L to about 0.25 g/L, and more preferably of from about 0.001 g/L to about 0.05 g/L.

The media of the invention may contain ascorbic acid as a selective agent. Ascorbic acid has inhibitory activity against some species of *Citrobacter*. See U.S. Pat. No. 4,279,995 to Woods et al. Ascorbic acid may be included in the media at a concentration of from about 0.05 g/L to about 20 g/L, preferably of from about 0.1 g/L to about 10 g/L, and more preferably of from about 0.5 g/L to about 2.0 g/L.

The media of the invention may contain bromobenzoic acid as a selective agent. Bromobenzoic acid has inhibitory activity against some species of *Citrobacter*. See U.S. Pat. No. 4,279,995 to Woods et al. Bromobenzoic acid may be included in the media at a concentration of from about 0.001 g/L to about 1.0 g/L, preferably of from about 0.002 g/L to about 0.50 g/L, and more preferably of from about 0.01 g/L to about 0.10 g/L.

The media of the invention may contain myricetin as a selective agent. Myricetin inhibits *Enterobacter* and *Klebsiella* spp. Brilliant green inhibits many commensal *E. coli* but surprisingly has no effect against Shiga toxin-producing *E. coli* or *Salmonella* at concentrations of about 1 mg/L. Myricetin may be included in the media at a concentration of from about 0.001 g/L to about 1.0 g/L, preferably of from about 0.002 g/L to about 0.50 g/L, and more preferably of from about 0.01 g/L to about 0.10 g/L. Lower concentrations may be preferred for selection of Shiga toxin-producing *E. coli*.

The media of the invention may contain nitrofurantoin as a selective agent. Nitrofurantoin is 1-[[(5-Nitro-2-furanyl)methylene]amino]-2,4-imidazolidinedione and is available under Cat. No. N7878 from Sigma-Aldrich Co., St. Louis, Mo. Nitrofurantoin is typically used to treat urinary tract infection, and is often used against *E. coli*. As shown in the following examples, nitrofurantoin is surprisingly ineffective against Shiga toxin-producing *E. coli* and *Salmonella* and can therefore be used to select for these microorganisms. The nitrofurantoin may be included in the media at a concentration of from about 0.0001 g/L to about 0.1 g/L, preferably of from about 0.0005 g/L to about 0.05 g/L, and more preferably of from about 0.001 g/L to about 0.01 g/L.

The media of the invention may contain one or more rifamycins as a selective agent. Suitable rifamycins include rifamycins A, B, C, D, E, S, and SV as well as the rifamycin derivatives rifampicin (or rifampin), rifabutin, rifapentine, and rifalazil. Rifampicin is preferred. The rifamycin may be included in the media at a concentration of from about 0.0001 g/L to about 0.2 g/L, preferably of from 0.0002 g/L to about 0.1 g/L, and more preferably of from 0.001 g/L to about 0.02 g/L.

The media of the invention may contain one or more polyketides as a selective agent. Suitable polyketides include macrolide antibiotics such as pikromycin, erythromycin A, clarithromycin, and azithromycin; polyene antibiotics such as amphotericin; tetracycline; and doxacycline. Tetracycline and/or doxycycline are preferred. The polyketide may be included in the media at a concentration of from about 0.0001 g/L to about 0.2 g/L, preferably of from 0.0002 g/L to about 0.1 g/L, and more preferably of from 0.001 g/L to about 0.02 g/L.

The media of the invention may contain one or more oxazolidinones as a selective agent. Suitable oxazolidinones include linezolid (ZYVOX®, Pfizer, Inc., New York, N.Y.), posizolid, torezolid, radezolid (RX-1741), and cycloserine. Linezolid is preferred. The oxazolidinone may be included in the media at a concentration of from about 0.0001 g/L to about 0.2 g/L, preferably of from 0.0002 g/L to about 0.1 g/L, and more preferably of from 0.001 g/L to about 0.02 g/L.

Some media of the invention comprise only one of a sulfa drug, a surfactant, an aminocoumarin, cycloheximide, a supravital stain, ascorbic acid, bromobenzoic acid, myricetin, nitrofurantoin, a rifamycin, a polyketide, or an oxazolidinone as a selective agent. Some media of the invention comprise a sulfa drug in combination with any one, all, or subcombinations of a surfactant, an aminocoumarin, cycloheximide, a supravital stain, ascorbic acid, bromobenzoic acid, myricetin, nitrofurantoin, a rifamycin, a polyketide, and an oxazolidinone as a selective agent. Some media of the invention comprise a surfactant in combination with any one, all, or subcombinations of a sulfa drug, an aminocoumarin, cycloheximide, a supravital stain, ascorbic acid, bromobenzoic acid, myricetin, nitrofurantoin, a rifamycin, a polyketide, and an oxazolidinone as a selective agent. Some media of the invention comprise an aminocoumarin in combination with any one, all, or subcombinations of a sulfa drug, a surfactant, cycloheximide, a supravital stain, ascorbic acid, bromobenzoic acid, myricetin, nitrofurantoin, a rifamycin, a polyketide, and an oxazolidinone as a selective agent. Some media of the invention comprise cycloheximide in combination with any one, all, or subcombinations of a sulfa drug, a surfactant, an aminocoumarin, a supravital stain, ascorbic acid, bromobenzoic acid, myricetin, nitrofurantoin, a rifamycin, a polyketide, and an oxazolidinone as a selective agent. Some media of the invention comprise a supravital stain in combination with any one, all, or subcombinations of a sulfa drug, a surfactant, an aminocoumarin, cycloheximide, ascorbic acid, bromobenzoic acid, myricetin, nitrofurantoin, a rifamycin, a polyketide, and an oxazolidinone as a selective agent. Some media of the invention comprise ascorbic acid in combination with any one, all, or subcombinations of a sulfa drug, a surfactant, an aminocoumarin, cycloheximide, a supravital stain, bromobenzoic acid, myricetin, nitrofurantoin, a rifamycin, a polyketide, and an oxazolidinone as a selective agent. Some media of the invention comprise bromobenzoic acid in combination with any one, all, or subcombinations of a sulfa drug, a surfactant, an aminocoumarin, cycloheximide, a supravital stain, ascorbic acid, myricetin, nitrofurantoin, a rifamycin, a polyketide, and an oxazolidinone as a selective agent. Some media of the invention comprise myricetin in combination with any one, all, or subcombinations of a sulfa drug, a surfactant, an aminocoumarin, cycloheximide, a supravital stain, ascorbic acid, bromobenzoic acid, nitrofurantoin, a rifamycin, a polyketide, and an oxazolidinone as a selective agent. Some media of the invention comprise nitrofurantoin in combination with any one, all, or subcombinations of a sulfa drug, a surfactant, an aminocoumarin, cycloheximide, a supravital stain, ascorbic acid, bromobenzoic acid, myricetin, a rifamycin, a polyketide, and an oxazolidinone as a selective agent. Some media of the invention comprise a rifamycin in combination with any one, all, or subcombinations of a sulfa drug, a surfactant, an aminocoumarin, cycloheximide, a supravital stain, ascorbic acid, bromobenzoic acid, myricetin, nitrofurantoin, a polyketide, and an oxazolidinone as a selective agent. Some media of the invention comprise a polyketide in combination with any one, all, or subcombinations of a sulfa drug, a surfactant, an aminocoumarin, cycloheximide, a supravital stain, ascorbic acid, bromobenzoic acid, myricetin, nitrofurantoin, a rifamycin, and an oxazolidinone as a selective agent. Some media of the invention comprise an oxazolidinone in combination with any one, all, or subcombinations of a sulfa drug, a surfactant, an aminocoumarin, cycloheximide, a supravital stain, ascorbic acid, bromobenzoic acid, myricetin, nitrofurantoin, a rifamycin, and a polyketide as a selective agent.

The media of the invention may also contain one or more efflux pump inhibitors (EPIs). As used herein, "efflux pump inhibitor" refers to any agent capable of inhibiting a bacterial efflux pump. The EPI preferably increases the toxicity of selective agents in non-*Salmonella* and non-Shiga toxin-producing *E. coli* microorganisms.

Phylogenetically, bacterial antibiotic efflux pumps belong to five superfamilies (see reviews (Li X Z, Nikaido H. Efflux-mediated drug resistance in bacteria. Drugs 2004; 64:159-204) (Paulsen I T. Multidrug efflux pumps and resistance: regulation and evolution. *Curr Opin Microbiol* 2003; 6:446-51) (Saier M H Jr. Tracing pathways of transport protein evolution. Mol Microbiol 2003; 48:1145-56)), namely: (i) ABC (ATP-binding cassette), which are primary active transporters energized by ATP hydrolysis; (ii) SMR [small multidrug resistance subfamily of the DMT (drug/metabolite transporters) superfamily]; (iii) MATE [multi-antimicrobial extrusion subfamily of the MOP (multidrug/oligosaccharidyl-lipid/polysaccharide flippases) superfamily]; (iv) MFS (major facilitator superfamily); and (v) RND (resistance/nodulation/division superfamily), which are all secondary active transporters driven by ion gradients. The MFS and RND pumps are the most abundant. The MFS pumps are found in both Gram-positive and Gram-negative bacteria, and are characterized by a relative narrow spectrum, recognizing usually one or sometimes a few antibiotic classes; the RND pumps are found exclusively in Gram-negative bacteria and display an extremely wide spectrum of substrates (poly-selectivity), including not only several classes of antibiotics, but also antiseptic compounds, dyes, or detergents. See: (1) Levy S B. Active efflux, a common mechanism for biocide and antibiotic resistance. *J Appl Microbiol* 2002; 92 Suppl: 65-71; (2) Li X Z, Nikaido H. Efflux-mediated drug resistance in bacteria. Drugs 2004; 64:159-204; (3) Lomovskaya O, Totrov M. Vacuuming the periplasm. *J. Bacteriol* 2005; 187:1879-83; (4) Poole K. Efflux-mediated antimicrobial resistance. *J Antimicrob Chemother* 2005; 56:20-51; (5) Van Bambeke F, Glupczynski Y, Plesiat P, et al. Antibiotic efflux pumps in prokaryotic cells: occurrence, impact on resistance and strategies for the future of antimicrobial therapy. *J Antimicrob Chemother* 2003; 51:1055-65; (6) Koronakis V. TolC-the bacterial exit duct for proteins and drugs. *FEBS Lett* 2003; 555:66-71; and (7) Piddock L J. Clinically relevant chromosomally encoded multidrug resistance efflux pumps in bacteria. *Clin Microbiol Rev* 2006; 19:382-402.

Suitable EPIs that may be included in the media of the invention include phenothiazines (see Molnar J, Hever A, Fakla I, et al. Inhibition of the transport function of membrane proteins by some substituted phenothiazines in *E. coli* and multidrug resistant tumor cells. *Anticancer Res* 1997; 17:481-6), phenylpiperidines (see Kaatz G W, Moudgal V V, Seo S M, et al. Phenylpiperidine selective serotonin reuptake inhibitors interfere with multidrug efflux pump activity in *Staphylococcus aureus*. *Int J Antimicrob Agents* 2003; 22:254-61), tetracycline analogs (Nelson M L, Park B H, Andrews J S, et al. Inhibition of the tetracycline efflux antiport protein by 13-thio-substituted 5-hydroxy-6-deoxytetracyclines. *J Med Chem* 1993; 36:370-7; and Nelson M L, Park B H, Levy S B. Molecular requirements for the inhibition of the tetracycline antiport protein and the effect of potent inhibitors on the growth of tetracycline-resistant bacteria. *J Med Chem* 1994; 37:1355-61.), aminoglycoside analogs (Françoise Van Bambeke, Jean-Marie Pagès and Ving J. Lee. Inhibitors of Bacterial Efflux Pumps as Adjuvants in Antibiotic Treatments and Diagnostic Tools for Detection of Resistance by Efflux. *Recent Patents on Anti-Infective Drug Discovery,* 2006, 1, 157-175), fluoroquinolone analogs (Françoise Van Bambeke, Jean-Marie Pagès and Ving J. Lee. Inhibitors of Bacterial Efflux Pumps as Adjuvants in Antibiotic Treatments and Diagnostic Tools for Detection of Resistance by Efflux. *Recent Patents on Anti-Infective Drug Discovery,* 2006, 1, 157-175), quinoline derivatives (Mahamoud A, Chevalier J, Davin-Regli A, et al. Quinolone derivatives as promising inhibitors of antibiotic efflux pump in multidrug resistant *Enterobacter aerogenes*. *Curr Drug Targets* 2006; 7:843-7), peptidomimetics (Lomovskaya O, Bostian K A. Practical applications and feasibility of efflux pump inhibitors in the clinic—a vision for applied use. *Biochem Pharmacol* 2006; 71:910-18), pyridopyrimidines (Nakayama K, Ishida Y, Ohtsuka M, et al. MexAB-OprM-specific efflux pump inhibitors in *Pseudomonas aeruginosa*. Part 1: discovery and early strategies for lead optimization. *Bioorg Med Chem Lett* 2003; 13:4201-4; Nakayama K, Ishida Y, Ohtsuka M, et al.

MexAB-OprM specific efflux pump inhibitors in *Pseudomonas aeruginosa*. Part 2: achieving activity in vivo through the use of alternative scaffolds. *Bioorg Med Chem Lett* 2003; 13:4205-8; Nakayama K, Kawato H, Watanabe J, et al. MexAB-OprM specific efflux pump inhibitors in *Pseudomonas aeruginosa*. Part 3: Optimization of potency in the pyridopyrimidine series through the application of a pharmacophore model. *Bioorg Med Chem Lett* 2004; 14:475-9; Nakayama K, Kuru N, Ohtsuka M, et al. MexAB-OprM specific efflux pump inhibitors in *Pseudomonas aeruginosa*. Part 4: Addressing the problem of poor stability due to photoisomerization of an acrylic acid moiety. *Bioorg Med Chem Lett* 2004; 14:2493-7; and Yoshida K, Nakayama K, Kuru N, et al. MexAB-OprM specific efflux pump inhibitors in *Pseudomonas aeruginosa*. Part 5: Carbon-substituted analogues at the C-2 position. *Bioorg Med Chem* 2006; 14:1993-2004), arylpiperidines (Thorarensen A, Presley-Bodnar A L, Marotti K R, et al. 3-Arylpiperidines as potentiators of existing antibacterial agents. *Bioorg Med Chem Lett* 2001; 11:1903-6), and arylpiperazines (Bohnert J A, Kern W V. Selected arylpiperazines are capable of reversing multidrug resistance in *Escherichia coli* overexpressing RND efflux pumps. Antimicrob Agents Chemother 2005; 49:849-52; Schumacher A, Steinke P, Bohnert J A, et al. Effect of 1-(1-naphthylmethyl)-piperazine, a novel putative efflux pump inhibitor, on antimicrobial drug susceptibility in clinical isolates of Enterobacteriaceae other than *Escherichia coli*. *J Antimicrob Chemother* 2006; 57:344-8; Kern W V, Steinke P, Schumacher A, et al. Effect of 1-(1-naphthylmethyl)-piperazine, a novel putative efflux pump inhibitor, on antimicrobial drug susceptibility in clinical isolates of *Escherichia coli*. *J Antimicrob Chemother* 2006; 57:339-43; Pannek S, Higgins P G, Steinke P, et al. Multidrug efflux inhibition in *Acinetobacter baumannii*: comparison between 1-(1-naphthylmethyl)-piperazine and phenyl-arginine-beta-naphthylamide. *J Antimicrob Chemother* 2006; 57:970-4.). See also Mahamoud, A. et al. Antibiotic efflux pumps in Gram-negative bacteria: the inhibitor response strategy. *J. Antimicrob. Chemoth.* 59(6): 1223-1229. 2007.

Suitable phenothiazines include promethazine and 3,7,8,-trihydroxy-, 7,8-dihydroxy, 7,8-diacetoxy-, 7,8dimetoxy-, 7-semicarbazone-, and 5-oxo-chlorpromazine derivatives, among others. Suitable phenylpiperidines include the paroxetine isomer NNC 20-7052, among others. Suitable tetracycline analogs include 13-(alkylthio) and 13-(arylthio) derivatives of 5-hydroxy-6-deoxytetracycline, among others. Suitable aminoglycoside analogs include the aminoglycosides described in U.S. Pat. No. 7,829,543, among others. Suitable fluoroquinolone analogs include those described in WO0209758A2 and WO0209758A3, among others. Suitable quinoline derivatives include alkylamino-, alkylalkoxy-, thioalkoxy-, and halo-quinoline derivatives (e.g., chloroquinoline derivatives) and those having piperidinoethyl chains, among others. A preferred quinoline derivative is 4-chloroquinoline. Suitable peptidomimetics include MC-207 110 or phenylalanine arginyl β-naphthylamide (PAβN), and derivatives thereof, among others. Suitable arylpiperidines include 3-arylpiperidine derivatives, among others. Suitable arylpiperazines include arylpiperazines, including 1-(1-naphthylmethyl)piperazine and others.

The EPIs are preferably selected from the group consisting of arylpiperazines, such as 1-(1-naphthylmethyl)piperazine (NMP; CAS No. 40675-81-8; available as Cat. No. 651699, Sigma-Aldrich Co., St. Louis, Mo.), and quinoline derivatives, such as 4-chloroquinoline (4-CQ; CAS No. 611-35-8; available as Cat. No. C70509, Sigma-Aldrich Co., St. Louis, Mo.). The NMP and 4-CQ may be included individually or together.

As shown in the following Examples, combinations of an EPI with polyketide, rifamycin, or oxazolidinone antibiotics can increase the activity of these antibiotics against Enterobacteriacae and other microorganisms without substantially affecting growth and fermentation of *Salmonella* species and/or Shiga toxin-producing *E. coli* strains. Accordingly, the one or more selective agents and the efflux pump inhibitor are present in the media of the invention in amounts effective to inhibit growth of at least one non-*Salmonella* species and/or at least one non-Shiga toxin-producing *E. coli* strain to a greater extent than *Salmonella* species (such as *Salmonella enterica*) and/or Shiga toxin-producing *E. coli* strains. It is preferred that the combination of the one or more selective agents and the efflux pump inhibitor are present in an amount that does not substantially affect the growth or metabolism of *Salmonella* species (such as *Salmonella enterica*) and/or Shiga toxin-producing *E. coli* strains.

The media described herein can be provided in a hydrated form, such as in the form of a liquid or gel-like (e.g., agar) medium, or in a dried form. If in a dried form, the components are preferably present in a proportion such that addition of water or other solvents provides each of the components within the concentration ranges described above. In addition, the media, whether in died or hydrated form, may be provided in separate combinations, e.g., basal media and one or more supplements, as described in the following examples.

Methods of using the media of the invention are apparent from the following examples. The media of the invention can be used to select for *Salmonella* and/or Shiga toxin-producing *E. coli* from other microorganisms, the latter including *Citrobacter* spp. (e.g., *Citrobacter freundii*, *Citrobacter koseri*, etc.), non-Shiga toxin-producing *E. coli*, and/or commensal *E. coli* generally. The media of the invention can be used for detecting *Salmonella* and/or Shiga toxin-producing *E. coli*. Specifically, the media of the invention can be used for cultivating or selecting for *Salmonella* (including *Salmonella enterica*); cultivating or selecting for Shiga toxin-producing *E. coli* (including *E. coli* having a type selected from O157, O145, O104, O26, O111, O103, and O91); or co-cultivating or co-selecting for *Salmonella* (including *Salmonella enterica*) and Shiga toxin-producing *E. coli* (including *E. coli* having a type selected from O157, O145, O104, O26, O111, O103, and O91).

Kits for use of the media of the invention may include any combination of components described herein, such as in the following examples.

Concentrations other than those explicitly described herein, such as above and below the stated ranges, are included in the invention.

The elements and method steps described herein can be used in any combination whether explicitly described or not.

All combinations of method steps described herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the following claims.

EXAMPLES

The following working examples are intended to illustrate the features of the present invention without limiting the particular components or potential use of the media.

Example 1

*Salmonella* Indicator Broth-1 (SIB-1)

Several experiments were conducted with an EPI-supplemented medium, referred to herein as "SIB-1."

Example 1.1

Summary

The *Salmonella* Indicator Broth-1, (SIB-1), is a single step selective enrichment indicator broth to be used as simple screening test for the presence of *Salmonella* spp. in environmental samples. This test permits the end user to avoid the multi-step process of sample processing to identify presumptively positive samples as exemplified by standard U.S. reference methods. SIB-1 permits the outgrowth of *Salmonella* while inhibiting the growth of competitive gram-negative and gram-positive micro-flora. Growth of *Salmonella*-positive cultures results in a visual color change of the medium from purple to yellow when the sample is grown at 37±1° C.

Performance of SIB-1 was evaluated in five different categories: inclusivity-exclusivity, methods comparison, ruggedness, lot-to-lot variability, and shelf stability. The inclusivity panel included 100 different *Salmonella* serovars of which 98 were positive for SIB-1 during the 30 to 48 hour incubation period.

The exclusivity panel included 33 different non-*Salmonella* microorganisms of which 31 were SIB-1 negative during the incubation period.

Methods comparison studies included four different surfaces, *S. Newport* on plastic, *S. Anatum* on sealed concrete, *S. Abaetetuba* on ceramic tile and *S. Typhimurium* in the presence of one log excess of *C. freundii*. Results of the methods comparison studies demonstrated no statistical difference between the SIB-1 method and the FDA-BAM reference method, as measured by the Mantel-Haenszel chi-square test. The overall sensitivity relative to the reference method across all four surfaces was >100% (it is possible bacterial growth occurred during the study period). There were no significant differences between SIB-1 and the reference method on any of the surfaces tested.

Ruggedness studies demonstrated little variation in test results when SIB-1 incubation temperatures were varied over a six degree centigrade range, 34° C. to 40° C. Lot to lot consistency results suggests no detectable differences in manufactured goods using two reference *Salmonella* serovars and one non-*Salmonella* microorganism.

Example 1.2

Definitions

Relative Sensitivity: Defined as the number of samples testing positive by the SIB-1 method divided by the number of samples testing positive by the reference culture procedure.

Statistical Data Analysis: The Mantel-Haenszel chi-square formula for unmatched test portions was used for the statistical analysis (1). A Chi-square value <3.84 indicates that the proportions positive for the alternative and the reference method are not statistically different at the 5% level of significance. This criterion must be satisfied for each level of each surface type. However, a significant difference between the proportions positive for the two methods is acceptable provided that the alternative method demonstrates superior recovery to the reference method.

Example 1.3

Principle

The principle of SIB-1 utilizes two operating conditions, the first selective enrichment of the *Salmonella* population from the background microflora and secondly the simultaneous metabolism of a very specific *Salmonella* substrate. SIB-1 is a balanced blend of proprietary selective agents highly restrictive to non-*Salmonella* bacteria and combining a highly specific metabolic substrate for *Salmonella*. As the selected population grows out the media becomes acidified and an incorporated pH indicator detects the pH change by a color shift from purple to yellow.

Example 1.4

Preparation of Basal SIB Medium

Peptone 10 g/L, $MgCl_2$ hexahydrate 13 g/L, bromocresol purple 0.02 g/L, and sulfanilamide 0.9 g/L were dissolved in 950 mL de-ionized, distilled water; autoclaved under standard sterilization cycle conditions, 121° C. at 3 atm for 15 minutes; and cooled to about 30° C. The following components were then added as filter-sterilized supplements: sulfathiazole 0.1 g/L; NIAPROOF® 4 1.5 g/L; 2-deoxy-D-ribose 5 g/L; cycloheximide 0.05 g/L; ascorbic acid 1 g/L; p-bromobenzoic acid 0.04 g/L; novobiocin 0.02 g/L; brilliant green 0.001 g/L; and myricetin 0.03 g/L.

Example 1.5

Preparation of SIB-1

Basal SIB was supplemented with 1-(1-naphthylmethyl) piperazine (NMP) at a final concentration of 0.2 mM (0.044 g/L) to generate SIB-1.

Example 1.6

SIB-1 Kit Components

Kits for methods employing *Salmonella* selection and detection include 15-mL screw cap vials containing SIB-1.

The kits may also include 3M™ ENVIRO SWAB environmental sample collecting swabs, available through 3M Company (St. Paul, Minn.) or Paradigm Diagnostics, Inc. (St. Paul, Minn.), or equivalent. Alternatives include WHIRL-PAK® sampling bags (Nasco Industries, Inc., Fort Atkinson, Wis.) with pre-moistened carcass sponges, or equivalent.

Example 1.7

Incubations

Incubations were conducted in a temperature-thermostated incubator (preferred) or heating block (32° C. to 40° C.).

Example 1.8

Standard Reference Materials

Reference strains were obtained through the following sources, Microbiologics, Inc., St. Cloud, Minn., National Collection of Type Cultures (NCTC) Health Protection Agency Culture Collection, Porton Down, UK., Prof. Francisco Diez-Gonzalez, Department of Food Science, University of Minnesota, St. Paul, Minn., and the American type Culture Collection (ATCC), Bethesda, Md. Sero-groups were identified through reference to the handbook of *Salmonella* antigenic structures (Grimont, Patrick A. D. & Weill, Francois-Xavier. ANTIGENIC FORMULAE OF THE *SALMONELLA* SEROVARS. 2007, 9th edition).

Example 1.9

General Sample Preparation

Pure cultures were obtained from Health Protection Agency, NCTC, Porton Down, UK and Microbiologics, Inc., St. Cloud, Minn., the University of Pennsylvania School of Veterinary Medicine, Center for Reference *Salmonella* and Microbiology Labs of Dr. Diez and Dr. Feirtag at the University of Minnesota, St. Paul, Minn. Original pure cultures were grown overnight in sterile Tryptic Soy Broth (TSB) or Brain Heart Infusion broth (BHI) at 32-37° C. In order to have reproducible cultures, 50% glycerol stock solutions of cultures were prepared and stored in a freezer. Fifty percent glycerol stock cultures were prepared by diluting 500 µL of pure culture grown overnight with 500 µL sterile glycerol. Then 200 µL portions were filled into sterile 2 mL centrifuge tubes, capped and kept in a freezer at −15° C. until the day before use. On the day before use, a loop-full of freezer-stored stock cultures were inoculated into 5 mL of sterile TSB, the same loop was streaked onto tryptic soy agar (TSA). The plates were incubated overnight at 37±1° C. TSA plates were checked for visible contamination, based on colony morphology. If the TSA plates suggested there was no visible contamination, logarithmic level dilutions were made into sterile peptone solutions (0.1% peptone water). Aliquots containing 100 µL of 6 and 7 log dilutions from overnight cultures were plated onto TSA for estimating the cell concentration (CFU/mL) and checked for contamination.

Dilutions of pure cultures aforementioned were used for inclusivity-exclusivity, method comparison, ruggedness and lot to-lot variability, and shelf stability studies.

Example 1.10

Environmental Sample Preparation and Analysis

Environmental samples were taken with sampling devices following U.S. FDA Bacteriological Analytical Manual (BAM) recommendations for sampling (U.S. Food and Drug Administration (2011) Bacteriological Analytical Manual, Chapter 5). The sampling devices were returned back into the original sterile container. One unit (15 mL) of SIB-1 media was aseptically added to each sterile container to fully submerge the applicator tip and was incubated in an upright position for 30 to 48 hours at 37±1° C. The color of the media was checked. The sample was called presumptive positive for *Salmonella* if the color of the media changed from purple color to a yellow color.

In order to confirm the negatives, purple/pale colorless-colored (presumptive negative) tubes were incubated for a total of 48 hours. At least one negative control was run in each set of analysis. A negative control was an unused sampling device containing one unit of SIB-1, incubated alongside the samples.

Example 1.11

Inclusivity-Exclusivity Studies

Serial dilutions from overnight grown pure cultures of 100 different *Salmonella* and 33 different non-*Salmonella* cultures were made into sterile 0.1% peptone water. One hundred microliters from log −8 dilution (~1.0E+3 CFU/mL) were plated onto TSA plates for estimating the number of cells tested. For the inclusivity studies 0.1 mL (estimated cell amount ranging from 10 to 100 CFU of *Salmonella*) of a dilution aliquot was aseptically transferred onto the top of the sampling sponge. For the exclusivity studies 0.2 mL (estimated cell amount >1,000,000 CFU of non-*Salmonella*) of a dilution aliquot was aseptically transferred onto the top of the sampling sponge. The sampling device was placed back into the sterile tube and submerged in 15 mL of SIB-1 media. The results are given in Tables 1-1 and 1-2 respectively.

TABLE 1-1

Results of Inclusivity Test for SIB-1

| Serovar | Source | Origin | SIB-1 Medium Color | Presumptive Result | Serogroup |
| --- | --- | --- | --- | --- | --- |
| S. Adelaide | U of MN 94679420 | Meat meal | Yellow | + | O |
| S. Agona | U of MN inv 95650951 | Soybean meal | Yellow | + | B |
| S. Albany | U of MN 2009595 | Frozen fish paste | Yellow | + | C3 |
| S. Anatum | U of MN 95645854 | Chicken feed | Yellow | + | E1 |

TABLE 1-1-continued

Results of Inclusivity Test for SIB-1

| Serovar | Source | Origin | SIB-1 Medium Color | Presumptive Result | Serogroup |
|---|---|---|---|---|---|
| S. Bovismorbificans | U of MN 3064124 | Vietnam | Yellow | + | C2 |
| S. Carrau | U of MN 2003413 | Frozen shrimp | Yellow | + | H |
| S. Cerro | U of MN 94713965 | Poultry feed | Yellow | + | K |
| S. Cubana | U of MN 94679421 | Swine feed | Blue | | G2 |
| S. Chester | U of MN 3063650 | Frozen tilapia fish | Yellow | + | B |
| S. Emek | U of MN 3063892 | Frozen catfish | Yellow | + | C3 |
| S. Enteritidis | U of MN 95657613 | Ice cream | Yellow | + | D1 |
| S. Give | U of MN 1829352 | Lobster tail | Yellow | + | E1 |
| S. Gloucester | U of MN 1676771 | Sesame seeds | Yellow | + | B |
| S. Hvittingfoss | U of MN 200373 | Frozen frog legs | Yellow | + | I |
| S. Infantis | U of MN 2015422 | Frozen lobster tail | Yellow | + | C1 |
| S. Javiana | U of MN 1842147 | Frozen shrimp | Yellow | + | D1 |
| S. Kentucky | U of MN 95-690-012 | Cottonseed | Yellow | + | C3 |
| S. Lille | U of MN 95-713-959 | Chicken feed | Yellow | + | C1 |
| S. Mbandaka | U of MN 95690014 | Soybean meal | Yellow | + | C1 |
| S. Meleagridis | U of MN 1949345 | Frozen shrimp | Yellow | + | E1 |
| S. Montevideo | U of MN 95573493 | Raw eggs | Yellow | + | C1 |
| S. Muenchen | U of MN 1842204 | Frozen shrimp | Yellow | + | C2 |
| S. Newbrunswick | U of MN 1842304 | Frozen shrimp | Yellow | + | E1 |
| S. Nashua | U of MN 2006036 | Poultry feed | Yellow | + | M |
| S. Newport | U of MN 2006038 | Frozen lobster tail | Yellow | + | C2 |
| S. Penilla | U of MN 1949289 | Frozen shrimp | Yellow | + | M |
| S. Poona | U of MN 1103174 | White pepper | Yellow | + | G1 |
| S. Sterrenbos | U of MN 1842082 | Frozen shrimp | Yellow | + | C3 |
| S. Thompson | U of MN 95657618 | Ice cream | Yellow | + | C1 |
| S. Weltevreden | U of MN 1950358 | Dried ling shrimp | Yellow | + | E1 |
| S. Typhimurium | U of MN 3019907 | Salted dune egg | Yellow | + | B |
| S. Worthington | U of MN 95-713-958 | Chicken feed | Yellow | + | G2 |
| S. Kumasi | U of MN 1929854 | Frozen crab meat | Yellow | + | N |
| S. Rubislaw | U of MN 2004976 | Frozen shrimp | Yellow | + | F |
| S. Goodwood | U of MN | Faeces | Yellow | + | E4 |
| S. Senftenberg | U of MN | Sewage | Yellow | + | E4 |
| S. Ohio | U of MN | Animal feed | Yellow | + | C1 |
| S. Limete | U of MN | | Yellow | + | B |
| S. Tennessee | U of MN | Soybean meal | Yellow | + | C1 |
| S. Newington | U of MN | Wild poultry | Yellow | + | B |
| S. Aberdeen | NCTC 5791 | Infantile diarrhea | Yellow | + | F |
| S. Aequatoria | NCTC 7891 | African zoonosis | Yellow | + | C1 |
| S. Alabama | NCTC 9868 | Human faeces | Yellow | + | B |
| S. Altendorf | NCTC 10546 | | Yellow | + | B |
| S. Austin | NCTC 8447 | | Yellow | + | C1 |
| S. Ball | NCTC 9870 | | Yellow | + | B |

TABLE 1-1-continued

Results of Inclusivity Test for SIB-1

| Serovar | Source | Origin | SIB-1 Medium Color | Presumptive Result | Serogroup |
|---|---|---|---|---|---|
| S. Berkeley | NCTC 8260 | Diseased turkey | Yellow | + | U |
| S. Brookfield | NCTC 10946 | | Yellow | + | O66 |
| S. California | NCTC 6018 | Animal feed | Yellow | + | B |
| S. Canastel | NCTC 6948 | Animal feed | Yellow | + | D1 |
| S. Carmel | NCTC 9872 | Infantile diarrhea | Yellow | + | O17 |
| S. Champaign | NCTC 6851 | Hen liver | Yellow | + | Q |
| S. Chicago | NCTC 9873 | | Yellow | + | M |
| S. Colombo | NCTC 9922 | Sheep | Yellow | + | P |
| S. Ealing | NCTC 11949 | Dried baby milk | Yellow | + | O |
| S. Dahlem | NCTC 9949 | Cattle | Yellow | + | Y |
| S. Gallinarum | NCTC 10532 | Poultry | Blue | − | D1 |
| S. Houten | NCTC 10401 | Reptile | Yellow | + | O43 |
| S. Kottbus | NCTC 5753 | Faeces | Yellow | + | C2 |
| S. Illinois | NCTC 8498 | Poults | Yellow | + | E3 |
| S. Lexington | NCTC 6244 | Soybean | Yellow | + | E1 |
| S. Manchester | NCTC 7372 | | Yellow | + | C2 |
| S. Minnesota | NCTC 5800 | Swine | Yellow | + | L |
| S. Mississippi | NCTC 6487 | Faeces | Yellow | + | G2 |
| S. Napoli | NCTC 6853 | Food handlers | Yellow | + | D1 |
| S. Pensacola | NCTC 6946 | | Yellow | + | D1 |
| S. Pretoria | NCTC 6234 | Meat | Yellow | + | F |
| S. Shanghai | NCTC 9791 | | Yellow | + | I |
| S. Sunsvall | NCTC 9787 | Dried egg | Yellow | + | H |
| S. Waycross | NCTC 7401 | Urine | Yellow | + | S |
| S. Alachua | U Penn STS 6 | Swine | Yellow | + | O |
| S. Choleraesuis | ATCC 10708 | Fish | Yellow | + | C |
| S. Arkansas | U Penn STS 11 | | Yellow | + | B |
| S. Blockley | U Penn STS 15 | Environment | Yellow | + | C2 |
| S. Brandenburg | U Penn STS 18 | Swine | Yellow | + | B |
| S. Derby | U Penn STS 22 | Polluted water | Yellow | + | B |
| S. Dublin | U Penn STS 27 | Cattle | Yellow | + | D1 |
| S. Hadar | U Penn STS 45 | Turkey | Yellow | + | C2 |
| S. Heidelberg | U Penn STS 48 | Poultry | Yellow | + | B |
| S. London | U Penn STS 64 | Polluted water | Yellow | + | E1 |
| S. Manhattan | U Penn STS 65 | Avian | Yellow | + | C2 |
| S. Oranienburg | U Penn STS 83 | Egg | Yellow | + | C1 |
| S. Panama | U Penn STS 86 | Infantile diarrhea | Yellow | + | D1 |
| S. Paratyphis | ATCC 13314 | Sewage | Yellow | + | A |
| S. Saint Paul | U of MN | Milk powder | Yellow | + | B |
| S. Schwarzengrund | U Penn STS 95 | Chicken | Yellow | + | B |
| S. Stanley | U Penn STS100 | Reptile | Yellow | + | B |
| S. Urbana | U Penn STS110 | Reptile | Yellow | + | N |
| S. Johannesburg | U Penn STS 56 | Meat meal | Yellow | + | R |
| S. Thomasville | U Penn STS103 | Poultry meal | Yellow | + | E3 |
| S. Virchow | U Penn STS 112 | Basil | Yellow | + | C1 |
| S. Abaetetuba | ATCC 35640 | Fresh water | Yellow | + | F |
| S. Choleraesuis var. Kunzendorf | ATCC 12011 | Swine | Yellow | + | B |
| S. Vallore | ATCC 15611 | | Yellow | + | B |
| S. Paratyphis | U of MN 2014696 | Frozen frog legs | Yellow | + | B |
| S. Tallahassee | ATCC 12002 | | Yellow | + | C3 |
| S. Salford | U of MN 2009532 | Oregano turkey | Yellow | + | I |
| S. Birmingham | U of MN DI95764802 | Alfalfa seed | Yellow | + | E1 |
| S. Brunei | U of MN 1680318 | Frozen Shrimp | Yellow | + | C3 |
| S. Ikeja | U of MN 3019543 | Frozen Shrimp | Yellow | + | E1 |
| S. Cubana | UPenn | Swine | Yellow | + | G2 |

TABLE 1-2

Results of Exclusivity Test for SIB-1

| Species | Source | Origin | SIB-1 Result |
|---|---|---|---|
| Klebsiella pneumoniae | NCTC 9633 | Sputum | − |
| Proteus mirabilis | ATCC 12453 | GI tract | − |
| Citrobacter freundii | NCTC 9750 | Soil | − |
| Escherichia coli | ATCC 13706 | GI tract | − |
| Escherichia coli | ATCC 14948 | GI tract | − |
| Hafnia alvei | ATCC 700025 | Brewery fermentation samples | − |
| Serratia liquefaciens | ATCC 27592 | | − |
| Morganella morganii subsp. morganii | ATCC 25829 | | − |
| Pseudomonas aeruginosa | ATCC 10145 | | − |
| Providencia rettgeri | ATCC 9250 | | − |
| Enterobacter amnigenus | ATCC 51816 | | − |
| Enterobacter aerogenes | ATCC 13048 | | − |
| Shigella sonnei | ATCC 25931 | | − |
| Shigella flexneri | ATCC 9199 | | − |
| Staphylococcus epidermidis | ATCC 14990 | | − |
| Staphylococcus aureus | ATCC 700699 | | − |
| Serratia marcescens | ATCC 13880 | Polenta | − |
| Enterobacter cloacae subsp. cloacae | ATCC 23355 | | − |
| Enterobacter gergoviae | ATCC 33028 | | − |
| Klebsiella oxytoca | ATCC 13182 | | − |
| Providencia wickerhamii | ATCC 16529 | | − |
| Shigella boydii | ATCC 9207 | | − |
| Staphylococcus aureus | NCTC 12973 | | − |
| Yersinia enterocolitica subsp. enterocolitica | ATCC 23715 | | − |
| Yersinia ruckerii | ATCC 29473 | | − |
| Citrobacter freundii | ATCC 8090 | | + |
| Citrobacter braakii | ATCC 43162 | | − |
| Citrobacter koseri | ATCC 27156 | | + |
| Escherichia coli | NCIMB 11943 | | − |
| Escherichia coli | NCTC 10538 | | − |
| Listeria monocytogenes | ATCC 13932 | | − |
| Listeria innocua | ATCC 33090 | | − |
| Pasteurella multocida subsp. multocida | ATCC 12945 | | − |
| Providencia stuartii | ATCC 33672 | | − |
| Edwardsiella tarda | ATCC 15947 | | − |

Example 1.12

Methods Comparison Studies

Method comparison studies were done for four different *Salmonella* species paired with four different common food environmental surfaces; S. Abaetetuba on ceramic tiles, S. Anatum on sealed concrete, *S. Newport* on plastic surface, and *S. Typhimurium* in the presence of one log excess *C. freundii* on stainless steel.

Example 1.12.1

FDA-BAM Method

The FDA-BAM method calls for a multi-step procedure as described. Following the 2 hour holding period after sampling, 3M™ ENVIROSWAB environmental sample collecting swabs were transferred to sterile stomacher bags and enriched with 225 mL of Lactose broth. The samples were allowed to stand for 60±5 minutes at room temperature and then incubated for 24±2 hours at 35±1° C. No pH adjustment was necessary prior to incubation. After incubation, 0.1 mL of primary enrichment for each sample was transferred to 10 mL of Rappaport-Vasilliadis medium (RV) and 1.0 mL to 10 mL of Tetrathionate (TT) broth. The RV broth was incubated at 42±1° C. for 24±2 hours and the TT broth was incubated at 35±1° C. for 24±2 hours. Following incubation, a loopful (10 μL) of each secondary enrichment was streaked to bismuth sulfate (BS), xylose lysine desoxycholate (XLD), and Hektoen enteric (HE) selective agars and incubated at 35±1° C. for 24±2 hours. The BS plates that were negative at 24 hours were then re-incubated for an additional 24 hours at 35±1° C. A suspect colony from each selective agar was picked and stabbed to Triple Sugar Iron (TSI) agar and Lysine Iron Agar (LIA) plates and streaked to a tryptic soy agar (TSA) plate. The TSI, LIA, and TSA plates were incubated at 35±1° C. for 24±2 hours. Growth from each TSA plate was used to conduct the polyvalent somatic 0 serological test, MICROGEN™ SALMONELLA LATEX test (Microgen Bioproducts Ltd., Surrey, UK) and biochemical tests for confirmation. Final confirmations were conducted with MICROGEN™ GN-ID biochemical panels (Microgen Bioproducts Ltd., Surrey, UK).

Example 1.12.2

SIB-1 Method

Following the 2 hour holding period after sampling, excess DE neutralizing broth from the swab tubes (3M™ ENVIROSWAB) was removed and 15 mL of *Salmonella* Indicator Broth was added to the swab tube. The samples were then incubated at 37±1° C. for 24-48 hours. After 24 hours, each sample was examined for presumptive positive results (broth color change from blue to yellow). Presumptive positives at 24 hours were streaked to the reference agars for the specified reference method and re-incubated for an additional 24 hours. Positive and negative samples, yellow and purple respectively were streaked onto XLD, HE and BS and followed through to confirmation as described for the FDA-BAM method.

Example 1.12.3

S. Newport on Plastic Surface

Serial logarithmic dilutions of overnight culture of S. Newport in BHI were made into sterile BHI. A one-hundred μL volume of log −7 and log −8 dilutions was plated onto TSA plates for estimating the number of cells loaded onto 4"×4" zones on plastic. Polypropylene plastic cutting boards were bought from a local department store. 4"×4" zones were marked on the surface of the cutting boards. They were wrapped in aluminum foil and autoclaved for 15 min at 120° C. Plastic cutting boards were kept wrapped until the time of inoculation. 1 The inoculation of surfaces were done at 0.5 mL/4"×4" surface from the log −7 (high) and log-8 (low) dilutions, corresponding approximately to 2.18 log CFU and 1.18 log CFU of *S. Newport* consecutively, twenty replicates for each level per method. Inoculations on surfaces were spread within the corresponding 4"×4" zone with the help of a disposable sterile spreader. After that surfaces were left to dry min 18 hours at room temperature. After the samples were dried on the surfaces for a minimum of 18 hours, they were removed by swabbing using 3M™ ENVIROSWAB environmental sample collecting swabs saturated with ten mL of DE broth. Both test method (SIB-1) and reference method (FDA-BAM) was done in twenty replicates per level (high and low) of inoculations. In order to confirm the presence of Salmonella in all test samples, all samples were streaked onto HE, XLD and BS agar after at the end of 48th hour at 37±1° C. Dark green colonies grown on HE were selected and processed as described for GN-ID analysis and polyvalent somatic 0 serological tests. Five un-inoculated samples were assayed. The summary of the data for S. Newport on plastic is given in Table 2.

As seen from Table 2, SIB-1 was comparable to the reference method. The reference method gave two more positives at the low level than the test method. Although the Chi Square values indicated that the test method and the reference method were not significantly different at the low level.

Example 1.12.4

S. Anatum on Sealed Concrete

S. Anatum stock culture grown overnight in BHI. Serial logarithmic dilutions of S. Anatum were made into sterile BHI. A one-hundred μL volume of log −7 and log −8 dilutions were plated onto TSA plates for estimating the number of cells loaded onto 4"×4" zones on sealed concrete blocks. Concrete blocks (15.5"×7.5"×3.5"; length×width× depth) were purchased from a local HOME DEPOT® supply store. Blocks were sealed with a solvent-based concrete sealer (BW Crete Seal 25 LV, St. Paul, Minn.). After a minimum of two coats of sealant was placed on the blocks, they were dried in a chemical hood until all the solvent had evaporated (minimum of 24 hours). Zones of 4"×4" were marked on the sealed side using a permanent marker. Before inoculations, sealed concrete blocks were sprayed with ethanol and allowed to air dry. The ethanol was air dried for at least minutes but no more than an hour. The inoculation of sealed concrete surfaces were done at 0.5 mL/surface from the log-7 S. Anatum (high) and log-8 S. Anatum (low) dilutions, corresponding approximately to 2.22 log CFU and 1.25 log CFU respectively, twenty replicates for each level, per method. Inoculations on surfaces were spread within the corresponding 4"×4" zone. Surfaces were left to dry for at least 18 hours at room temperature.

After the samples were dried on the surfaces for a minimum of 18 hours, they were removed by swabbing using 3M™ ENVIROSWAB environmental sample collecting swabs. Both test methods SIB-1 method and reference method (FDA-BAM) were done in twenty replicates per level (high and low) of inoculations. Five un-inoculated samples were assayed.

Table 2 shows the reference method identified a single sample more than the test method at the low level. Accordingly chi square values suggested that there was no significant difference between the test method and the reference method at both of the levels tested.

Example 1.12.5

S. Abaetetuba on Ceramic Tile

Serial logarithmic dilutions of overnight culture of S. Abaetetuba in BHI were made into sterile BHI. Aliquots containing 100 μL of log −8 and log −9 dilutions were plated onto TSA plates for estimating the number of cells loaded onto 4"×4" ceramic tiles. Ceramic tiles at 4×4 inches in dimensions were bought from a local Home Depot. They were wrapped in aluminum foil and autoclaved for 15 min at 121° C. All tiles were kept wrapped at room temperature until the time of inoculation.

The inoculation of surfaces was done at 0.50 mL/4"×4" surface from the log −8 (high) and log-9 (low) dilutions, corresponding approximately to 1.67 log CFU and 0.60 log CFU respectively, twenty replicates for each level, per method. Inoculations on surfaces were spread within the corresponding 4"×4" zone with the help of sterile spreaders. Surfaces were left to dry for at least 18 hours at room temperature. After the samples were dried on the surfaces for a minimum of 18 hours, they were removed by swabbing using the 3M™ ENVIROSWAB swabs. Both the test method (SIB-1) and the reference method (FDA-BAM) were done in twenty replicates per level (high and low) of inoculations. Five un-inoculated samples were assayed.

In order to confirm the presence-absence of Salmonella in all test samples, all tubes of SIB-1 were streaked onto HE, XLD and BS plates at the end of 48th hour of incubation. Dark green colonies with grown on HE were processed as described for immunoassay and GN-ID analysis for confirmation. Summary of the data for S. Abaetetuba on tile is given in Table 2.

As seen from the Table 2 below, SIB-1 was slightly more sensitive than the reference method. The reference method resulted in fewer positives 7 versus 10, than the test method at the low level. Chi-square value also showed that the two methods were not significantly different from each other at the low level testing.

Example 1.12.6

Independent Laboratory Surface Comparison Study: S. Typhimurium: C. freundii on Stainless Steel For the analysis of stainless steel surfaces, a total of 45 samples for both the SIB-1 and FDA/BAM were analyzed for method comparison. Within each sample set there were 20 low-level, 20 high-level, and 5 un-inoculated samples. The target levels of S. Typhimurium ATCC#14028 used for challenging the stainless steel surfaces were as follows: 1-50 CFU/4"×4" (100 cm$^2$) surface area for the low-level samples, 50-100 CFU/4"×4" (100 cm$^2$) surface area for the high-level samples, and 0 CFU/4"×4" (100 cm$^2$) surface area for the un-inoculated control samples. Additionally, the surfaces were inoculated with C. freundii ATCC#8090 at 10 times the level of the S. Typhimurium to simulate the performance of the target organism in the presence of a competing microflora. The inocula were prepared in Brain Heart Infusion Broth (BHI) incubated for 24±2 hours at 37±1° C. Following incubation, the broth inocula were serial diluted using BHI until the target inoculum level was reached. The stainless steel surfaces were inoculated with 0.25 mL from both the *S. Typhimurium* and *C. freundii* inocula and then allowed to dry at ambient temperature for 16-24 hours.

Results obtained from the stainless steel environmental surfaces assayed by the SIB-1 method were comparable to those analyzed by the FDA/BAM reference method for the detection of *Salmonella*. See Table 1-3 A Mantel-Haenszel chi-square analysis for unmatched test portions between the SIB-1 method and the reference method produced a value of 2.05 for the low-level test portions and a value of 0.61 for the high-level test portions.

The values obtained for the matrix indicate that there was no statistically significant difference between the number of confirmed positive results obtained by the two methods being compared at both levels, 5 positives for the SIB-1 method compared to 3 positives for the FDA-BAM procedure.

TABLE 1-3

Summary of Method Comparison Studies of SIB at 48 Hour Incubation

| Matrix | Strain | $N^a$ | SIB-1 Presumptive Pos. | SIB-1 Confirmed Pos. | FDA-BAM Positive | Chi Square$^b$ | Relative Sensitivity$^c$ |
|---|---|---|---|---|---|---|---|
| Plastic | *S. Newport* | 5 | 0 | 0 | 0 | — | — |
| | | 20 Low level | 11 | 11 | 13 | 0.406 | 84.6% |
| | | 20 High level | 20 | 20 | 20 | 0 | 100% |
| Sealed concrete | *S. Anatum* | 5 | 0 | 0 | 0 | — | — |
| | | 20 Low level | 7 | 7 | 8 | 0.104 | 87.5% |
| | | 20 High level | 20 | 20 | 20 | 0 | 100% |
| Ceramic tile | *S. Abaetetuba* | 5 | 0 | 0 | 0 | — | — |
| | | 20 Low level | 10 | 10 | 7 | 0.898 | 142.9% |
| | | 20 High level | 20 | 20 | 20 | 0 | 100% |
| Stainless steel$^d$ | *S. Typhimurium*: 10X *C. freundii* | 5 | 0 | 0 | 0 | — | — |
| | | 20 Low level | 0 | 0 | 2 | 2.05 | 0 |
| | | 20 High level | 5 | 5 | 3 | 0.609 | 166.7% |

$^a$N = Number of test portions
$^b$Chi Square = Mantel-Haenszel: $\chi^2 = (n-1)(ad-bc)^2/[(a+b)(a+c)(b+d)(c+d)]$, where n = total number of samples tested by the two methods, a = number of samples positive by the test method, b = number of samples negative by the test method, c = number of samples positive by the reference method and d = number of samples negative by the reference method
$^c$Relative sensitivity = a/c, where a = number of samples confirmed positive by the test method and c = number of samples positive by the reference method
$^d$Trial performed at the independent laboratory

Example 1.12.7

Ruggedness Studies

Ruggedness parameters studied were: incubation times (28 hours, 32 hours and 46 and 50 hours) and incubation temperatures (34 and 40±1° C.). Two positive controls (*S. Abaetetuba* and *S. Anatum*) and one negative control (*E. coli*) were tested in 5 replicates at the 3 log CFU/mL for *Salmonella* serovars and at 7 log CFU/mL for *E. coli*. These tests were done on different days as recommended. The summary of the results is given in Tables 1-4 and 1-5.

TABLE 1-4

Temperature Variability

| Strain | 24 Hour 34° C. | 24 Hour 37° C. | 24 Hour 40° C. | 48 Hour 34° C. | 48 Hour 37° C. | 48 Hour 40° C. |
|---|---|---|---|---|---|---|
| *S. Abaetetuba* | | | | | | |
| A | + | + | + | + | + | + |
| B | + | + | + | + | + | + |
| C | + | + | + | + | + | + |
| D | + | + | + | + | + | + |
| E | + | + | + | + | + | + |
| *S. Anatum* | | | | | | |
| A | + | + | − | + | + | + |
| B | + | + | − | + | + | + |
| C | + | + | − | + | + | + |
| D | + | + | − | + | + | + |
| E | + | + | − | + | + | + |
| *E. coli* | | | | | | |
| A | − | − | − | − | − | − |
| B | − | − | − | − | − | − |
| C | − | − | − | − | − | − |
| D | − | − | − | − | − | − |
| E | − | − | − | − | − | − |

TABLE 1-5

Time Variability

| Strain | 18 Hour | 24 Hour | 52 Hour |
|---|---|---|---|
| *S. Abaetetuba* | | | |
| A | + | + | + |
| B | + | + | + |
| C | + | + | + |
| D | + | + | + |
| E | + | + | + |
| *S. Anatum* | | | |
| A | + | + | + |
| B | + | + | + |
| C | + | + | + |
| D | + | + | + |
| E | + | + | + |
| *E. coli* | | | |
| A | − | − | − |
| B | − | − | − |
| C | − | − | − |
| D | − | − | − |
| E | − | − | − |

Example 1.13

Lot-to-Lot Variability and Shelf Stability

Lot to lot variability studies were done in 5 replicates per level of each microorganism (*S. Abaetetuba* ATCC 35640, *S. Anatum* ATCC 9270 and *E. coli* ATCC 14948) for each of the three production lots tested (Table 4a). One hundred microliters of culture dilutions were inoculated onto the tip of a 3M™ ENVIROSWAB environmental sample collecting swab, which was then fully submerged into 15 mL of SIB-1 in its original sterile container and incubated at 37° C. for 48 hours. The summary of the results is given in Tables 1-6 and 1-7.

TABLE 1-6

Lot Variability

| Strain | Lot 06007 | Lot 06009 | Lot 06011 |
|---|---|---|---|
| *S. Abaetetuba* | | | |
| A | + | + | + |
| B | + | + | + |
| C | + | + | + |
| D | + | + | + |
| E | + | + | + |
| *S. Anatum* | | | |
| A | + | + | + |
| B | + | + | + |
| C | + | + | + |
| D | + | + | + |
| E | + | + | + |
| *E. coli* | | | |
| A | − | − | − |
| B | − | − | − |
| C | − | − | − |
| D | − | − | − |
| E | − | − | − |

TABLE 1-7

Shelf Stability

| Strain | Lot 06007 30 Days | Lot 06007 60 days | Lot 06007 90 days |
|---|---|---|---|
| *S. Abaetetuba* | | | |
| A | + | + | + |
| B | + | + | + |
| C | + | + | + |
| D | + | + | + |
| E | + | + | + |
| *S. Anatum* | | | |
| A | + | + | + |
| B | + | + | + |
| C | + | + | + |
| D | + | + | + |
| E | + | + | + |
| *E. coli* | | | |
| A | − | − | − |
| B | − | − | − |
| C | − | − | − |
| D | − | − | − |
| E | − | − | − |

Example 1.14

Analysis of Additional Real Environmental Samples

Environmental samples were obtained from food and non-food contact surfaces in a coffee processing facility. Fifteen milliliters of SIB-1 was added to the samples and incubated at 37° C. for 48 hours and the SIB reaction was recorded. All samples were streaked onto two differential selective agar media: (1) xylose lysine tergitol-4 (XLT) agar medium (see SS in Table 5 below); and (2) bismuth sulfide agar medium (see BS in Table 5 below)). *Salmonella*-like colonies were picked for biochemical characterization using the MICROGEN™ GN-ID test (Microgen Bioproducts Ltd., Surrey, UK). All SIB-negative samples were confirmed to be negative on the differential selective agar media. The presumptive positive samples in the SIB yielded confirmed *Salmonella* species and two false positive samples, *Citrobacter freundii* and *E. coli* inactive. The data are shown in Table 1-8:

TABLE 1-8

Growth and Fermentation of Environmental Samples in SIB-1

| Sample ID | SIB Rxn | SS Agar | BS Agar | GNID(Microgen) |
|---|---|---|---|---|
| C1 | + | Lactose | + | *C.freundii* |
| C2 | − | NG | NG | |
| C3 | − | NG | NG | |
| C4 | − | NG | NG | |
| C5 | + | Lactose −, H2S | + | *Salmonella* spp. |
| C6 | + | Lactose −, H2S | + | *S.arizona* |
| C7 | + | Lactose −, H2S | + | *S.arizona* |
| C8 | − | NG | NG | |
| C9 | − | NG | NG | |
| C10 | + | Lactose + | + | *E. coli* inactive |
| C11 | − | NG | NG | |
| C12 | − | NG | NG | |
| C13 | − | NG | NG | |
| C14 | − | NG | NG | |
| C18 | − | NG | NG | |
| C19 | − | NG | NG | |
| C20 | − | NG | NG | |
| C21 | − | NG | NG | |
| C23 | + | Lactose w | + | *C.freundii* |

NG = No growth.
Lactose − = Lactose non-fermenter.
Lactose + = Lactose fermenter.
Lactose w = Lactose weak fermenter.
H$_2$S = Hydrogen sulfide producer.

Example 1.15

Discussion

SIB-1 is an easy to use and interpret screening test for *Salmonella* species in environmental samples. Inclusivity and exclusivity studies revealed that SIB-1 is very comprehensive for the detection of *Salmonella* species at very low levels (10-100 CFU/sample). Two strains, *S. Cubana* and *S. Gallinarum*, were originally negative in the inclusivity study. An additional isolate of *S. Cubana* was obtained from a different source, the University of Pennsylvania *Salmonella* Reference Center. This particular isolate was positive in fermenting the indicator compound in SIB-1 in contrast to the isolate obtained from the University of Minnesota's culture collection. These data suggest that the Minnesota isolate was likely defective in a metabolic pathway for fermentation of the indicator compound. In regard to specificity, high levels of some *Citrobacter* species remain to be a possible source of false positive results. False positive results, although not desired by the typical end user, still tells a great deal about the overall microbial cleanliness of the areas sampled. Learning about the presence of *Citrobacter* species is important for another aspect, since many *Citrobacter* species occupy similar niches to *Salmonella* species and arise as contamination sources from the GI tracts of warm blooded animals. This information is potentially useful when monitoring food processing surfaces intended to be free of microflora after sanitation operations. These results demonstrate a cross reaction in two of three *Citrobacter* species tested underscoring the need to confirm all SIB-1-positive results by the traditional biochemical or genetic methods.

SIB-1 was found to be at least as sensitive as the reference method in all the surfaces studied. In fact SIB-1 was slightly more sensitive than the reference method in one of the method comparison studies: five positives for SIB-1 versus three positives for the FDA-BAM method in the stainless steel study.

Regarding the ruggedness studies, recommended parameters have been studied for SIB-1. Results of the ruggedness studies suggested that for the most part, selected deviations from test parameters did not interfere with the true detection of microorganisms selected with the exception of *Salmonella* Anatum, which was not detected at 40° C. at 24 hours incubation.

Lot-to-lot variability studies showed that there was no difference between the production lots. Shelf life studies documented in Table 4b revealed that SIB-1 is shelf-stable at 3 months of refrigerated storage.

In conclusion, SIB-1 is a unique, easy to perform rapid detection test for *Salmonella* species in environmental samples. The test has been demonstrated to be substantially equivalent to the FDA-BAM method for the four selected surfaces as well as both sufficiently *Salmonella*-inclusive and exclusive with the notable exception of some *Citrobacter* species. These studies detail the utility of SIB-1 as diagnostic screening test. Since SIB-1 is a self-contained test, it minimizes cross contamination. Furthermore, this study shows that SIB-1 is compatible with the FDA-BAM confirmation methods. This compatibility provides a more economical solution to *Salmonella* screening without any compromise in sensitivity. It is expected that SIB-1 will enable more on-site *Salmonella* monitoring in the environmental samples and thereby contribute to the overall goal of raising food safety standards in the processing environment.

Example 2

SIB-1 Supplemented with Doxycycline

To increase the specificity of SIB-1, SIB-1 was supplemented with 0.005 g/L doxycycline. Sponges were inoculated at 10-100 CFU/Sample. The culture response of twenty *Salmonella enterica* serovars was recorded after 48 hours incubation at 37° C. The results are shown in Table 2-1.

TABLE 2-1

Inclusivity of SIB-1 Supplemented with Doxycycline

| *Salmonella enterica* serovar | *Salmonella* Indicator Broth Reaction |
|---|---|
| *S. Aberdeen* | + |
| *S. Aequatoria* | + |
| *S. Alabama* | + |

TABLE 2-1-continued

Inclusivity of SIB-1 Supplemented with Doxycycline

| Salmonella enterica serovar | Salmonella Indicator Broth Reaction |
|---|---|
| S. Altendorf | + |
| S. Austin | + |
| S. Ball | + |
| S. Berkeley | + |
| S. Brookfield | + |
| S. California | + |
| S. Canastel | + |
| S. Carmel | + |
| S. Carrau | + |
| S. Champaign | + |
| S. Chicago | + |
| S. Colombo | + |
| S. Ealing | + |
| S. Dahlem | + |
| S. Gallinarum | + |
| S. Houten | + |
| S. Kottbus | + |

These results show that adding doxycycline to SIB-1 does not inhibit *Salmonella* spp. growth.

Example 3

SIB-1 Supplemented with Rifampicin

To increase the specificity of SIB-1, SIB-1 was supplemented with 0.002 g/L rifampicin. Sponges were inoculated at 10-100 CFU/Sample. The culture response of twenty *Salmonella enterica* serovars was recorded after 48 hours incubation at 37° C. The results are shown in Table 3-1:

TABLE 3-1

Inclusivity of SIB-1 Supplemented with Rifampicin

| Salmonella enterica serovar | Salmonella Indicator Broth Reaction |
|---|---|
| S. Illinois | + |
| S. Lexington | + |
| S. Manchester | + |
| S. Minnesota | + |
| S. Mississippi | + |
| S. Napoli | + |
| S. Pensacola | + |
| S. Pretoria | + |
| S. Shanghai | + |
| S. Sunsvall | + |
| S. Carmel | + |
| S. Carrau | + |
| S. Champaign | + |
| S. Chicago | + |
| S. Colombo | + |
| S. Ealing | + |
| S. Dahlem | + |
| S. Gallinarum | − |
| S. Houten | + |
| S. Kottbus | + |
| S. Johannesberg | + |
| S. Oranienberg | + |
| S. Thomasville | + |
| S. Brandenburg | + |
| S. Manhattan | + |
| S. Urbana | + |
| S. Stanley | + |
| S. Panama | + |
| S. Cerro | + |
| S. Hadar | + |

These results show that supplementing SIB-1 with rifampicin does not inhibit *Salmonella* spp. growth.

Example 4

Antibiotic-Supplemented Basal SIB with and without NMP

To demonstrate the increased specificity of EPI-supplemented medium, four non-*Salmonella* species giving positive reactions in basal SIB or SIB-1 were tested in doxycycline-supplemented (0.005 g/L doxycycline), rifampicin-supplemented (0.002 g/L rifampicin), or linezolid-supplemented (0.005 g/L linezolid) basal SIB with and without 0.2 mM (0.044 g/L) 1-(1-naphthylmethyl)piperazine (NMP). The cultures were grown to stationary phase in BHI medium overnight at 37° C. and serially diluted out 3-log orders to obtain suspensions with approximately $10^5$-$10^6$ CFU/mL. One tenth milliliter was pipetted onto a sterile collection sponge (3M™ ENVIROSWAB) and 15 mL of the basal SIB supplemented with either antibiotic alone or antibiotic with NMP was added. The samples were incubated for 48 hours at 37° C. and the color reactions were recorded. The results are shown in Tables 4-1 through 4-3:

TABLE 4-1

Exclusivity of Doxycyline-Supplemented Basal SIB with and without NMP

| Species | Salmonella Indicator Broth Reaction Basal Media + Doxycycline | Salmonella Indicator Broth Reaction Basal Media + Doxycycline/NMP |
|---|---|---|
| Enterobacter aerogenes | + | − |
| Enterobacter cloacae | + | − |
| Citrobacter freundii | + | + |
| Citrobacter koseri | + | + |

TABLE 4-2

Exclusivity of Rifampicin-Supplemented Basal SIB with and without NMP

| Species | Salmonella Indicator Broth Reaction Basal Media + Rifampicin | Salmonella Indicator Broth Reaction Basal Media + Rifampicin/NMP |
|---|---|---|
| Enterobacter aerogenes | + | − |
| Enterobacter cloacae | + | − |
| Citrobacter freundii | + | − |
| Citrobacter koseri | + | − |

TABLE 4-3

Exclusivity of Linezolid-Supplemented Basal SIB with and without NMP

| Species | Salmonella Indicator Broth Reaction Basal Media + Linezolid | Salmonella Indicator Broth Reaction Basal Media + Linezolid/NMP |
|---|---|---|
| Enterobacter aerogenes | + | − |
| Enterobacter cloacae | + | − |
| Citrobacter freundii | + | − |
| Citrobacter koseri | + | − |

These results show that the effectiveness of the EPI in enhancing the selectivity of *Salmonella* spp. selective agents.

Example 5

Demonstration of *Salmonella*-Selective EPI Activity of 4-Chloroquinoline

To increase the specificity of basal SIB, basal SIB was supplemented with 4-chloroquinoline (4CQ) at a final concentration of 0.2 mM (0.023 g/L) and 0.002 g/L rifampicin. Sponges were inoculated at 10-100 CFU/Sample. The culture response of twenty *Salmonella enterica* serovars was recorded after 48 hours incubation at 37° C. The data are shown in Table 5-1:

TABLE 5-1

Inclusivity of Basal SIB Supplemented with Rifampicin and 4CQ

| *Salmonella enterica* serovar | *Salmonella* Indicator Broth Reaction |
|---|---|
| S. Aberdeen | + |
| S. Aequatoria | + |
| S. Alabama | + |
| S. Altendorf | + |
| S. Austin | + |
| S. Ball | + |
| S. Berkeley | + |
| S. Brookfield | + |
| S. California | + |
| S. Canastel | + |
| S. Carmel | + |
| S. Carrau | + |
| S. Champaign | + |
| S. Chicago | + |
| S. Colombo | + |
| S. Ealing | + |
| S. Dahlem | + |
| S. Gallinarum | + |
| S. Houten | + |
| S. Kottbus | + |

These results show that supplementing basal SIB with rifampicin and 4-chloroquinoline does not inhibit *Salmonella* spp. growth.

Example 6

Antibiotic-Supplemented Basal SIB with and without 4CQ

To further demonstrate the increased *Salmonella*-selective specificity of the EPI- and antibiotic-supplemented SIB, four non-*Salmonella* species giving positive reactions in basal SIB or SIB-1 were tested in the rifampicin-supplemented media (0.002 g/L rifampicin) with and without 4-chloroquinoline (4CQ). The cultures were grown to stationary phase in BHI medium overnight at 37° C. and serially diluted out 3-log orders to obtain suspensions with approximately $10^5$-$10^6$ CFU/mL. One tenth milliliter was pipetted onto a sterile collection sponge (3M™ ENVIROSWAB) and 15 mL of the basal SIB supplemented with either antibiotic alone or antibiotic with 4CQ was added. The samples were incubated for 48 hours at 37° C. and the color reactions were recorded. The data are shown in Table 6-1:

TABLE 6-1

Exclusivity of Rifampicin-Supplemented Basal SIB with and without 4CQ

| Species | *Salmonella* Indicator Broth Reaction Basal Media + Rifampicin | *Salmonella* Indicator Broth Reaction Basal Media + Rifampicin/4CQ |
|---|---|---|
| Enterobacter aerogenes | + | − |
| Enterobacter cloacae | + | − |
| Citrobacter freundii | + | − |
| Citrobacter koseri | + | − |

These results show that the effectiveness of 4CQ in enhancing the selectivity of *Salmonella* spp. selective agents.

Example 7

Discussion

Several media formulations were tested for permitting growth of *Salmonella* while inhibiting growth of non-*Salmonella* species. Initial media formulations lacking myricetin, antibiotics, and EPIs did not effectively inhibit the growth of some cross-reacting species, notably, *K. ozaenae, E. aerogenes, C. freundii, C. koseri* and *E. coli* inactive. To minimize the potential of such environmental microflora to contribute to false positive reactions in selective indicator media, flavonoid compounds were investigated. Myricetin was tested as a potential suitable inhibitor for at least some of these gram negative species. Myricetin was observed to be effective against *K. oxytoca* and *E. aerogenes* but was of little use against the *Citrobacter* and *E. coli* inactive isolates. Media supplemented with the halo-quinoline 4-chloroquinoline (4CQ) or the naphthylmethyl piperazine 1-(1-naphthylmethyl)piperazine (NMP) in combination with certain antibiotics were substantially effective in preventing outgrowth of all the *E. coli* inactive isolates and some of the Citrobacters, particularly *C. freundii*.

Particularly effective media formulations included the components contained in the basal selective indicator broth discussed below (including myricetin), an EPI (i.e., either halo-quinolines such as 4-chloroquinoline or naphthylmethyl piperazines such as 1-(1-naphthylmethyl)piperazine), and tetracycline, doxycycline, rifampicin, or linezolid. Such media were capable of controlling most of the gram negative competitors found in the environment, excluding some *C. koseri* strains. Compositions including rifampicin in place of tetracycline or doxycycline were highly inhibitory to all the *Citrobacter* species in the culture collection.

The data collectively demonstrate the enhancement of antimicrobial activity of selective agents in the presence of the EPIs. As shown herein, these agents effectively inhibit the growth of gram-negative competitors of *Salmonella* while not inhibiting the growth and metabolism of *Salmonella*.

Example 8

Selection Shiga Toxin-Producing *E. coli* from Commensal *E. coli*

Example 8.1

Background

The examples above show selective enrichment media for isolation and detection of *Salmonella* species. The examples that follow show use of similar compositions for the selection of Shiga toxin-producing *E. coli* (STEC). Since the late 1980's, commercial products have been developed for the isolation and detection of *E. coli* O157:H7 due the widespread food contamination events with this pathogen. Proliferation of other pathogenic *E. coli* serotypes has prompted regulators to require screening for a wider array of STEC species. Dubbed the "big Six" serotypes, *E. coli* strains O26, O111, O45, O145, O121, O103 in addition to O157 must now be screened for in meat processing within the United States. There remains no effective selective enrichment medium sufficiently restrictive to most other gram negative bacteria but permissive to growth of these *E. coli* serotypes.

Example 8.2

SIB-2

A variant of SIB-1, referred to as SIB-2, was generated. The composition of SIB-2 is shown in Table 8-1.

TABLE 8-1

| SIB-2 Composition | |
|---|---|
| Component | Concentration |
| Peptone | 10 g/L |
| MgCl₂ hexahydrate | 13 g/L |
| Bromocresol purple | 0.02 g/L |
| Sulfanilamide | 1 g/L |
| Sulfathiazole | 0.1 g/L |
| NIAPROOF ® 4 | 2 mL/L (2.12 g/L) |
| 2-Deoxy-D-ribose | 5 g/L |
| Cycloheximide | 0.05 g/L |
| Ascorbic acid | 1 g/L |
| p-Bromobenzoic acid | 0.04 g/L |
| Novobiocin | 0.02 g/L |
| Brilliant green | 0.001 g/L |
| Myricetin | 0.03 g/L |
| Naphthylmethyl piperazine (NMP) | 0.044 g/L |
| Doxycycline | 0.005 g/L |

Example 8.3

Inclusivity and Exclusivity Studies

Shiga toxin-producing *E. coli* (STEC) cultures were obtained from the Penn State University *E. coli* Reference Center. Determinations for the presence of the Shiga toxin genes (stx1 and stx2) were conducted at the Penn State University *E. coli* Reference Center. Serial dilutions from overnight grown pure cultures of STEC strains were made into sterile 0.1% peptone water. One hundred microliters from log −8 dilution (~1.0E+3 CFU/mL) were plated onto brain heart infusion (BHI) plates for estimating the number of cells tested. For inclusivity studies, 0.1 mL (estimated cell amount ranging from 10 to 100 CFU of STEC) of a dilution aliquot was aseptically transferred onto the top of the sampling sponge. For exclusivity studies, 0.2 mL (estimated cell amount >1,000,000 CFU of non-STEC) of a dilution aliquot was aseptically transferred onto the top of the sampling sponge. The sampling sponge was then placed back into the sterile tube and submerged in 15 mL of SIB-2 media. The growth of the STEC and non-STEC strains is shown in Table 8-2.

TABLE 8-2

| *E. coli* Strain Growth in SIB-2 Media | | | |
|---|---|---|---|
| *E. coli* Strain | Shiga Toxin | Cultural response in SIB | 2-DeoxyD-Ribose |
| O104:H4 | ND (presumptive +) | G | − |
| O26:H1 | + | G | − |
| O103:H2 | + | G | − |
| O91:H21 | ND (presumptive +) | G | − |
| O157:H7 | + | G | − |
| O145:H28 | + | G | − |
| O111:H8 | + | G | + |
| ATCC 13706 | ND (presumptive −) | NG | |
| ATCC 14948 | ND (presumptive −) | NG | |
| NCIMB 11943 | ND (presumptive −) | NG | |
| NCTC 10538 | ND (presumptive −) | NG | |

Table 8-2 documents the ability of seven different STEC serovars to grow in the presence of the selective agents present in SIB-2 media. By contrast none of the commensal *E. coli* strains inoculated at substantially higher inocula levels were capable of growth in SIB media. Most of the active STEC strains were incapable of fermenting the incorporated 2-deoxy D-ribose in the media. A more suitable fermentable substrate would likely be lactose because most *E. coli* strains are active lactose fermenters while most *Salmonella* species are negative for lactose fermentation.

Example 8.4

Selection of STEC from Bovine Manure in Feed Lots

To further expand the data set on the relative selectivity of the SIB-2 media for Shiga toxin-producing *E. coli* strains versus commensal *E. coli*, a series of *E. coli* isolates originally obtained from bovine manure in feed lots were examined. The isolates were obtained from Dr. Francisco Diez-Gonzalez, Department of Food Science and Nutrition, University of Minnesota. Table 8-3 provides a summary of the strain isolate biotypes.

TABLE 8-3

| *E. coli* Provenance | | |
|---|---|---|
| *E. coli* Strain | Shiga Toxin | Origin |
| O157:H7 | + | Penn State *E. coli* Ref. Center |
| O145:H28 | + | Penn State *E. coli* Ref. Center |
| O104:H4 | ND (presumptive +) | Penn State *E. coli* Ref. Center |
| O26:H1 | + | Penn State *E. coli* Ref. Center |
| O111:H8 | + | Penn State *E. coli* Ref. Center |
| O103:H2 | + | Penn State *E. coli* Ref. Center |
| O91:H21 | ND (presumptive +) | Penn State *E. coli* Ref. Center |
| 261 | − | University of MN |
| K12-W3110 | − | University of MN |
| A11-3 | ND (presumptive −) | University of MN |
| DH5-a | − | University of MN |
| 3TF1 | − | University of MN |

TABLE 8-3-continued

E. coli Provenance

| E. coli Strain | Shiga Toxin | Origin |
| --- | --- | --- |
| 3BF2 | ND (presumptive −) | University of MN |
| CR63 | − | University of MN |

Serial dilutions from overnight-grown pure cultures of the E. coli strains were made into sterile 0.1% peptone water. One hundred microliters from log −8 dilution (~1.0E+3 CFU/mL) were plated onto BHI plates for estimating the number of cells tested. Stock BHI cultures were diluted serially into 0.2 mL of SIB-2 media to obtain 5log dilutions yielding an initial inoculation concentration of between 100 to 1000 CFU/mL. Cultures were grown at 37° C. for 18 hours. Highest dilutions were streaked onto either BHI or selective differential agars for cell growth estimates.

Table 8-4 summarizes the cultural response of E. coli strains enriched in SIB-2. SIB-2 cultures were streaked onto BHI for growth estimates. From the data in Table 8-4 the SIB-2 medium permits growth of all the STEC isolates at low initial inoculation (<$10^3$ CFU/mL). By contrast the medium permits only three of the seven commensal E. coli strains from growing from low initial inoculations.

TABLE 8-4

Growth of E. coli Strains in SIB-2 Broth

| E. coli Strain | SIB Growth |
| --- | --- |
| O157:H7 | + |
| O145:H28 | + |
| O104:H4 | + |
| O26:H1 | + |
| O111:H8 | + |
| O103:H2 | + |
| O91:H21 | + |
| 261 | − |
| K12-W3110 | − |
| A11-3 | + |
| DH5-a | + |
| 3TF1 | + |
| 3BF2 | − |
| CR63 | + |

Example 8.5

Selection of STEC with SIB-2 Supplemented with Nitrofurantoin

To examine for the potential development of a more STEC-selective medium than SIB-2, we supplemented SIB-2 with 0.005 mg/L of nitrofurantoin, a broad spectrum antibiotic frequently used to treat E. coli urinary tract infections.

Table 8-5 summarizes the growth response of E. coli strains in SIB-2 supplemented with 0.005 g/L nitrofurantoin. As can be seen from the data in Table 8-5, supplementation of SIB-2 with nitrofurantoin renders the media more selective with respective to STEC strains. Whereas SIB-2 alone permitted growth of four of seven commensal E. coli strains, SIB-2 supplemented with nitrofurantoin excluded all but one of the commensal E. coli strains.

TABLE 8-5

Growth of E. coli Strains in SIB-2 Broth Supplemented with Nitrofurantoin

| E. coli Strain | SIB-2 Growth |
| --- | --- |
| O157:H7 | + |
| O145:H28 | + |
| O104:H4 | + |
| O26:H1 | + |
| O111:H8 | + |
| O103:H2 | + |
| O91:H21 | + |
| 261 | − |
| K12-W3110 | − |
| A11-3 | − |
| DH5-a | − |
| 3TF1 | + |
| 3BF2 | − |
| CR63 | − |

Example 9

Co-Selection of Salmonella and Shiga Toxin-Producing E. coli

An important trend in the meat industry in the United States is the ability to cultivate E. coli and Salmonella in the same selective enrichment media. Laboratories would like to streamline their processes by reducing the steps to regulatory compliance to one operation for screening for both E. coli and Salmonella. The examples above show the ability of the media of the invention to enrich for Shiga toxin-producing E. coli and Salmonella independently. The present example shows the ability of the media to support the growth of both pathogens through co-cultivation.

S. abetetuba obtained from the University of Pennsylvania Salmonella Reference Center was cultured in BHI overnight to obtain ~$10^{10}$ CFU/mL stock cultures. A comparable culture from each of the seven STEC strains shown in Tables 8-2 and 8-3 were also prepared and mixed with an equal volume (0.25 mL) of the Salmonella culture. An aliquot (0.02 mL) of each mixed culture was serially diluted out in SIB-2 eight log orders to obtain initial populations of $10^2$ to $10^3$ CFU/mL of each pathogen. The SIB-2 cultures were incubated for eighteen hours at 37° C. and streaked on an agar medium based on a variant of SIB-2 having the composition depicted in Table 9-1. The agar medium was supplemented with 5-bromo-4-chloro-3-indolyl-β-D-galactopyranoside (X-gal) and isopropyl β-D-1-thiogalactopyranoside (IPTG) to permit identification of the E. coli colonies (blue) from the Salmonella colonies (white). Growth results are summarized in Table 9-2.

TABLE 9-1

Agar Medium Composition

| Component | Concentration |
| --- | --- |
| Peptone | 10 g/L |
| MgCl$_2$ hexahydrate | 13 g/L |
| Sulfanilamide | 1 g/L |
| NIAPROOF ® 4 | 2 mL/L (2.12 g/L) |
| Cycloheximide | 0.05 g/L |
| Novobiocin | 0.02 g/L |
| Brilliant green | 0.001 g/L |
| Myricetin | 0.005 g/L |
| Naphthylmethyl piperazine | 0.044 g/L |
| Doxycycline | 0.005 g/L |

TABLE 9-1-continued

Agar Medium Composition

| Component | Concentration |
|---|---|
| Nitrofurantoin | 0.005 g/L |
| X-gal | 0.05 g/L |
| IPTG | 0.02 g/L |
| Agar | 15 g/L |

TABLE 9-2

Growth Results of Co-Cultivation

| E. coli Strain | Growth |
|---|---|
| O157:H7 | + |
| O145:H28 | − |
| O104:H4 | + |
| O26:H1 | + |
| O111:H8 | + |
| O103:H2 | + |
| O91:H21 | − |

The data show that after 24 hours of cultivation on the agar medium, five of seven STEC strains grew among a predominant population of S. abetetuba. After a further 24 hours, detectable blue colonies could be seen on both the O145 and O91 co-cultures in the presence of Salmonella background.

What is claimed is:

1. A selective enrichment medium for *Salmonella* or Shiga toxin-producing *E. coli* comprising:
a carbon and nitrogen source;
an inorganic salt;
a selective agent comprising one or more of a sulfa drug, a surfactant, an aminocoumarin, cycloheximide, myricetin, and nitrofurantoin and one or more of a rifamycin, a polyketide, and an oxazolidinone; and
an efflux pump inhibitor comprising one or more of 1-(1-naphthylmethyl)piperazine and 4-chloroquinoline.

2. The selective enrichment medium of claim 1 wherein the efflux pump inhibitor comprises 1-(1-naphthylmethyl)piperazine.

3. The selective enrichment medium of claim 1 wherein the efflux pump inhibitor comprises 4-chloroquinoline.

4. The selective enrichment medium of claim 1 wherein the selective agent comprises a sulfa drug, wherein the sulfa drug comprises one or more of sulfanilamide and sulfathiazole.

5. The selective enrichment medium of claim 1 further comprising one or more of a fermentable sugar, a supravital stain, ascorbic acid, and bromobenzoic acid, wherein the fermentable sugar comprises 2-deoxy-D-ribose and the supravital stain comprises brilliant green.

6. The selective enrichment medium of claim 1 wherein the selective agent comprises: a surfactant, wherein the surfactant comprises 7-ethyl-2-methyl-4-undecyl sulfate or a salt thereof; and an aminocoumarin, wherein the aminocoumarin comprises novobiocin.

7. The selective enrichment medium of claim 1 wherein the selective agent comprises a rifamycin, wherein the rifamycin comprises rifampicin.

8. The selective enrichment medium of claim 1 wherein the selective agent comprises a polyketide, wherein the polyketide comprises doxycycline.

9. The selective enrichment medium of claim 1 wherein the selective agent comprises an oxazolidinone, wherein the oxazolidinone comprises linezolid.

10. The selective enrichment medium of claim 1 wherein the selective agent comprises one or more of rifampicin, tetracycline, doxycycline, and linezolid.

11. The selective enrichment medium of claim 1 wherein the selective agent comprises a sulfa drug, a surfactant, an aminocoumarin, cycloheximide, myricetin, nitrofurantoin, and one or more of a rifamycin, a polyketide, and an oxazolidinone.

12. The selective enrichment medium of claim 1 further comprising a visual indicator that indicates the presence of a microorganism selected from the group consisting of *Salmonella* and *E. coli*.

13. The selective enrichment medium of claim 1 wherein the selective agent and the efflux pump inhibitor are present in amounts effective to inhibit growth of at least one non-*Salmonella* species to a greater extent than one or more *Salmonella* species.

14. A selective enrichment medium for *Salmonella* or Shiga toxin-producing *E. coli* comprising:
a carbon and nitrogen source;
an inorganic salt;
a selective agent comprising one or more of a sulfa drug, a surfactant, an aminocoumarin, cycloheximide, myricetin, nitrofurantoin, a rifamycin, a polyketide, and an oxazolidinone; and
an efflux pump inhibitor comprising one or more of 1-(1-naphthylmethyl)piperazine and 4-chloroquinoline,
wherein the selective agent and the efflux pump inhibitor are present in amounts effective to inhibit growth of at least one non-Shiga toxin-producing *E. coli* strain to a greater extent than one or more Shiga toxin-producing *E. coli* strains.

15. A method of selectively enriching for a microorganism selected from the group consisting of a *Salmonella* species and a Shiga toxin-producing *E. coli* strain, comprising culturing a sample suspected of containing the microorganism in the selective enrichment medium of claim 1.

16. The method of claim 15 wherein the culturing grows a *Salmonella* species, a Shiga toxin-producing *E. coli* strain, or both a *Salmonella* species and a Shiga toxin-producing *E. coli* strain.

17. The method of claim 16 further comprising detecting presence of the microorganism.

18. The selective enrichment medium of claim 1 wherein the selective agent and the efflux pump inhibitor are present in amounts effective to inhibit growth of at least one non-Shiga toxin-producing *E. coli* strain to a greater extent than one or more Shiga toxin-producing *E. coli* strains.

* * * * *